United States Patent [19]

MacDonald et al.

[11] Patent Number: 6,140,322
[45] Date of Patent: Oct. 31, 2000

[54] AMIDINE AND ISOTHIOUREA DERIVATIVES AS INHIBITORS OF NITRIC OXIDE SYNTHASE

[75] Inventors: James MacDonald, Pittsford; James Matz, Fairport; William Shakespeare, Rochester, all of N.Y.

[73] Assignee: Astra Aktiebolag, Sodertalje, Sweden

[21] Appl. No.: 09/233,476

[22] Filed: Jan. 20, 1999

Related U.S. Application Data

[63] Continuation of application No. 08/776,221, filed as application No. PCT/SE96/01425, Nov. 6, 1996.
[60] Provisional application No. 60/006,276, Nov. 7, 1995.

[30] Foreign Application Priority Data

Jan. 25, 1996 [SE] Sweden .................................. 9600275
Sep. 11, 1996 [SE] Sweden .................................. 9603300
Sep. 11, 1996 [SE] Sweden .................................. 9603301

[51] Int. Cl.[7] ........................ C07D 409/12; C07D 471/04; C07D 489/04; A61K 31/445
[52] U.S. Cl. ........................ 514/213; 514/214; 514/215; 514/220; 514/221; 540/558; 540/559; 540/560; 540/561; 540/562; 540/569; 540/570; 540/571; 540/572; 540/573
[58] Field of Search ........................ 540/558, 559, 540/560, 561, 562, 569, 570, 571, 572, 573; 514/213, 214, 215, 220, 221

[56] References Cited

U.S. PATENT DOCUMENTS 5,270,464 12/1993 Kukla et al. .............................. 540/556

FOREIGN PATENT DOCUMENTS

| 94/21621 | 9/1994 | WIPO . |
| 95/05363 | 2/1995 | WIPO . |
| 95/09619 | 4/1995 | WIPO . |
| 96/24588 | 8/1996 | WIPO . |

OTHER PUBLICATIONS

CAS Registry nos. cited against Claim 24:107393–74–8; 102599–10–0; 72299–68–4; 72299–67–3; 72232–26–9; 72232–25–8; 37481–24–6; 14788–34–2; 14097–41–7; 14097–40–6; and 14097–37–1.
CAS Registry nos. cited against Claim 26; 135043–75–3; 135007–64–6; 135007–60–2; 114166–30–2; 114166–29–9; 114166–17–5; 99365–69–2; 69062–43–7; 42923–79–5; 41959–45–9; 14097–36–0; and 14097–35–9.
C.R. Rasmussen et al; Improved Procedures for the Preparation of Cycloalkyl–, Arylalkyl–, and Arylthioureas; Synthesis, 1988 456–459.
Larsen et al "A Modified Bischler–Naprieralski Procedure for the Synthesis of 3–Aryl–3,4–dihyroisoquinolines" J. Org. Chem. 1991, 56, 6034–6038.
Brewer et al, "Synthesis and Anthelmintic Activity of a Series of Pyrazino[2,1–a] [2] benzazepine Derivatives" J Med. Chem. 1989, 32, 2058–2062.
Meyers "The Asymmetric Synthesis of 1–Alkyl–2,3,4, 5–Tetrahydro–Benzazeplnes and Benzo[β]–1–Azabicyclo [5,3,1] Descanes", Tetrahedron, 1993, 49, 1807–1820.
Bohme et al "Uber Derivate des 1,2,3,4, 5–Pentahydro–2–benzazepins"; Arch. Pharmazie 1973, 306, 271–274.
Edwards et al "A Convenient Synthesis of 1–Azabicycloalkanes and their Lactams Via Cuprates of Formamidines", Tetrahedron Letters, 1984, 25, 939–942.
Grunewald et al "Synthesis of 3–Alkyl–8–substituted–and 4–Hydroxy–8–substituted, –2,3,4, 5–tetrahydro–1H–2–benzazepines" J. Heterocyclic Chem., 1994, 31, 1609–1617.
Bredt "Isolation of nitric oxide synthetase, a calmodulin–requiring enzyme" Proc. Natl. Acad. Sci., 1990, 87, 682–685.
Haimova et al "One–Pot Synthesis of 5,6–Dihydro–8H–dibenzo[a,g]quinolizine–8–ones and Related Isoquinolines; A New Synthesis of Xylopinine" Synthesis, 1980, 845–847.
Coppola "Novel Hetercycles.8.Fused Isoquinolines Derived from the Reaction of Homophthalic Anhydride with Cyclic Imino Ethers", J Heterocyclic Chem., 1981, 18, 767–770.
Ernst Spath et al "Synthese von Isochinolin–Derivaten" Chem. Ber., 1930, 63B, 134–141.
San–ya Akaboshi et al, "Synthesis in the Benzoquinolizine Group . . . " Chem. Pharm. Bull., 1960, 8, 14–17.

*Primary Examiner*—Mukund J. Shah
*Assistant Examiner*—Bruck Kifle
*Attorney, Agent, or Firm*—Nixon & Vanderhye

[57] ABSTRACT

There are provided novel compounds of formula (I)

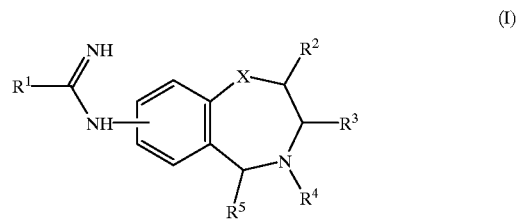

wherein X, $R^1$, $R^2$, $R^3$, $R^4$ and $R^5$ are as defined in the specification and optical isomers and racemates thereof and pharmaceutically acceptable salts thereof; together with processes for their preparation, compositions containing them and their use in therapy.

18 Claims, No Drawings

AMIDINE AND ISOTHIOUREA DERIVATIVES AS INHIBITORS OF NITRIC OXIDE SYNTHASE

This is a continuation of application Ser. No. 08/776,221, filed Jan. 22, 1997, now pending, which is a 371 of PCT/SE96/01425, filed Nov. 6, 1996.

This application claims benefit of Provisional Application 60/006,276 filed Nov. 7, 1995 and Provisional Application 60/006,253 filed Nov. 7, 1995.

This invention relates to new amidine and isothiourea derivatives, processes for their preparation, compositions containing them and their use in therapy.

According to the invention we provide a compound of formula (I)

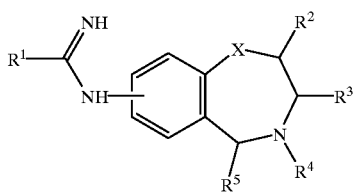

(I)

wherein:

X represents $NR^6$, S, O, $CH_2$ or a bond;
$R^1$ represents S-alkyl C1 to 3 or a five membered heterocyclic aromatic ring containing 1 to 4 heteroatoms selected from O, N and S optionally substituted at a carbon atom by one or more groups selected from halogen, trifluoromethyl, alkyl C1 to 6, nitro, or cyano;
$R^2$ represents hydrogen, alkyl C1 to 6, —$(CH_2)_d$OH, —$(CH_2)_d$OAr or —$(CH_2)_n$Ar;
$R^3$ represents hydrogen, alkyl C1 to 6, —$(CH_2)_b$OH, —$(CH_2)_b$OAr or —$(CH_2)_n$Ar;
$R^4$ represents hydrogen, alkyl C1 to 6, —$(CH_2)_c$OH, —$(CH_2)_c$OAr or —$(CH_2)_n$Ar;
$R^5$ represents hydrogen, alkyl C1 to 6, —$(CH_2)_q$OH, —$(CH_2)_q$OAr, —$(CH_2)_n$Ar, —$(CH_2)_t$COO$R^8$ or —$(CH_2)_t$CONR$^9$R$^{10}$;
or either $R^3$ and $R^4$ together or $R^4$ and $R^5$ together represent a chain —$(CH_2)_m$— or —$(CH_2)_r$Y$(CH_2)_p$—;
Ar represents a phenyl ring, a six membered heterocyclic aromatic ring containing one or two nitrogen atoms, or a five membered heterocyclic aromatic ring containing 1 to 4 heteroatoms selected from O, N and S, which phenyl ring, six membered heterocyclic aromatic ring or five membered heterocyclic aromatic ring may be optionally substituted by one or more groups selected from alkyl C1 to 6, alkoxy C1 to 6, halogen, nitro, cyano, perfluoroalkyl C1 to 6, phenyl or a five membered heterocyclic aromatic ring containing 1 to 4 heteroatoms selected from O, N and S;
Y represents O, S or $NR^7$;
m represents an integer 3 to 5;
r and p independently represent integers 1 to 3 save that r+p shall be in the range 2 to 4;
$R^6$, $R^7$, $R^8$, $R^9$ and $R^{10}$ independently represent hydrogen or alkyl C1 to 6;
or —$NR^9R^{10}$ together represent piperidinyl, pyrrolidinyl, morpholinyl, tetrahydroisoquinolinyl, piperazinyl, or piperazinyl 4-substituted by group $R^{15}$;
$R^{15}$ represents alkyl C1 to 6 or a group —$(CH_2)_w$Q;
Q represents phenyl optionally substituted by one or more groups selected from alkyl C1 to 6, alkoxy C1 to 6, halogen, nitro, cyano and trifluoromethyl;
n, w and d independently represent an integer 0 to 6;
h, q and b independently represent an integer 1 to 6;
c represents an integer 2 to 6;
t represents an integer 1 to 5;
provided that
(a) when X represents NH, O, $CH_2$ or a bond and at the same time $R^2$, $R^3$ and $R^5$ each represent hydrogen, then $R^4$ does not represent hydrogen or alkyl C1 to 6;
(b) when X represents $NR^6$, O or S, then d represents an integer 1 to 6;
and optical isomers and racemates thereof and pharmaceutically acceptable salts thereof.

We prefer that $R^1$ represents S-methyl or S-ethyl, especially S-ethyl, or a ring containing one heteroatom selected from O, N and S. We particularly prefer that $R^1$ represents thienyl, especially 2-thienyl.

Unless otherwise indicated, the term "alkyl C1 to 6" referred to herein denotes a straight or branched chain alkyl group having from 1 to 6 carbon atoms or a cyclic alkyl group having from 3 to 6 carbon atoms. Examples of such groups include methyl, ethyl, n-propyl, i-propyl, n-butyl, i-butyl, t-butyl, cyclopentyl and cyclohexyl.

Unless otherside indicated, the term "alkyl C1 to 3" referred to herein denotes a straight or branched chain alkyl group having from 1 to 3 carbon atoms. Examples of such groups include methyl, ethyl, n-propyl and i-propyl.

According to the invention, we further provide a process for the preparation of compounds of formula (I), and optical isomers and racemates thereof and pharmaceutically acceptable salts thereof, which comprises:

(a) preparing a compound of formula (I) by reacting a corresponding compound of formula (II)

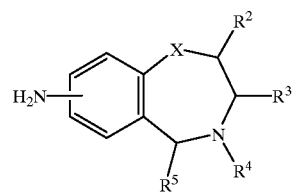

(II)

wherein X, $R^2$, $R^3$, $R^4$ and $R^5$ are as defined above, with a compound of formula (III)

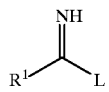

(III)

wherein $R^1$ is as defined above and L is a leaving group;

(b) preparing a compound of formula (I) by reacting a corresponding compound of formula (IV)

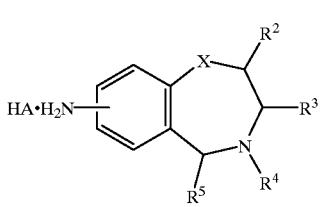

(IV)

wherein X, $R^2$, $R^3$, $R^4$ and $R^5$ are as defined above and HA is an acid, with a compound of formula (V)

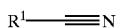 (V)

wherein $R^1$ is as defined above;

(c) preparing a compound of formula (I) wherein $R^1$ is S-alkyl C1 to 3 by reacting a corresponding compound of formula (VI)

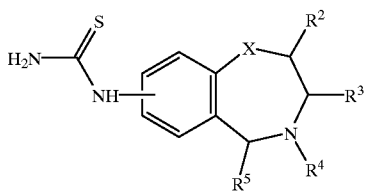 (VI)

wherein X, $R^2$, $R^3$, $R^4$ and $R^5$ are as defined above, with a compound of formula (VII)

 (VII)

wherein $R^{14}$ is alkyl C1 to 3 and L is a leaving group;

(d) preparing a compound of formula (I) in which $R^4$ represents alkyl C1 to 6, —$(CH_2)_c$OH, —$(CH_2)_c$OAr or —$(CH_2)_n$Ar by reacting a corresponding compound of formula (I) in which $R^4$ represents hydrogen with a compound of formula (VIII)

 (VIII)

wherein $R^{11}$ represents alkyl C1 to 6, —$(CH_2)_c$OH, —$(CH_2)_c$OAr or —$(CH_2)_n$Ar and L is a leaving group;

(e) preparing a compound of formula (I) in which X represents $NR^6$ and $R^6$ represents alkyl C1 to 6 by reacting a corresponding compound of formula (I) in which $R^6$ represents hydrogen with a compound of formula (IX)

 (IX)

wherein $R^{12}$ represents alkyl C1 to 6 and L is a leaving group;

(f) preparing a compound of formula (I) in which $R^3$ and $R^4$ or $R^4$ and $R^5$ are joined to form a chain —$(CH_2)_r$Y$(CH_2)_p$—; Y represents $NR^7$ and $R^7$ represents alkyl C1 to 6 by reacting a corresponding compound of formula (I) in which $R^7$ represents hydrogen with a compound of formula (IX);

(g) preparing a compound of formula (I) in which $R^5$ represents —$(CH_2)_s$COOR$^8$ and $R^8$ represents alkyl C1 to 6 by esterifying a corresponding compound of formula (I) in which $R^8$ represents hydrogen;

(h) preparing a compound of formula (I) in which $R^5$ represents —$(CH_2)_s$COOR$^8$ and $R^8$ represents hydrogen by hydrolysing a corresponding compound of formula (I) in which $R^8$ represents alkyl C1 to 6;

(i) preparing a compound of formula (I) in which $R^5$ represents —$(CH_2)_t$CONR$^9$R$^{10}$ and $R^9$ and/or $R^{10}$ represents alkyl C1 to 6 by alkylating a corresponding compound of formula (I) in which $R^9$ and/or $R^{10}$ represents hydrogen;

(j) preparing a compound of formula (I) in which $R^5$ represents —$(CH_2)_t$CONR$^9$R$^{10}$ in which $R^9$ and $R^{10}$ represent hydrogen or $R^5$ represents —$(CH_2)_s$COOR$^8$ and $R^8$ represents hydrogen by hydrolysis of the corresponding cyano compound;

(k) preparing a compound of formula (I) in which $R^5$ represents —$(CH_2)_t$CONR$^9$R$^{10}$ by reacting the corresponding amine HNR$^9$R$^{10}$ with the corresponding acid;

(l) preparing a compound of formula (I) in which $R^2$ represents —$(CH_2)_d$OAr, $R^3$ represents —$(CH_2)_b$OAr, $R^4$ represents —$(CH_2)_c$OAr or $R^5$ represents —$(CH_2)_q$OAr by reacting the corresponding halo or sulphonate compound of formula (I) with an aryl hydroxide;

(m) preparing a compound of formula (I) in which $R^4$ represents methyl by reacting a corresponding compound of formula (I) in which $R^4$ represents hydrogen with formaldehyde and formic acid; or (n) preparing a compound of formula (I) in which $R^4$ represents —$CH_2CH_2OH$ by reacting a corresponding compound of formula (I) in which $R^4$ represents hydrogen with oxirane;

and where desired or necessary converting the resultant compound of formula (I), or another salt thereof, to a pharmaceutically acceptable salt thereof, or vice versa.

In process (a), the reaction will take place on stirring a mixture of the reactants in a suitable solvent, for example N-methyl-2-pyrrolidinone or a lower alkanol e.g. ethanol, isopropanol or tertiary butanol, at a temperature between room temperature and the reflux temperature of the solvent. The reaction time will depend inter alia on the solvent and the nature of the leaving group, and may be up to 48 hours, however it will typically be from 1 to 5 hours. Suitable leaving groups that L may represent include thioalkyl, sulphonyl, trifluorocarbon sulphonyl, halide, alkyl and aryl alcohols and tosyl groups; others are recited in 'Advanced Organic Chemistry', J. March (1985) 3rd Edition, on page 315 and are well known in the art.

In process (b), the reaction is preferably performed by refluxing a mixture of the two compounds for several hours in the presence of a suitable solvent whereby the reaction temperature is high enough so that condensation takes place readily, but not sufficiently high to decompose the amidine formed. The reaction temperature can vary from room temperature to about 250° C., although it is preferable to perform the reaction at temperatures from about 100° C. to 200° C. We find that o-dichlorobenzene is a particularly suitable solvent and it is useful to add 4-dimethylaminopyridine as a catalyst. On cooling, two layers form, the solvent may be decanted, and the reaction worked up by addition of aqueous base. Alternatively, where the reactants are soluble in the solvent, the solvent may be evaporated off under vacuum and the reaction mixture worked up by addition of water. The acid HA may be an organic or inorganic acid, for instance, hydrochloric, hydrobromic, hydroiodic, sulphuric, nitric, phosphoric, acetic, lactic, succinic, fumaric, malic, maleic, tartaric, citric, benzoic or methanesulphonic acid. We prefer that HA is a hydrohalic acid.

In process (c) the reaction will proceed on combining the two reactants in an inert solvent e.g. acetone. Suitable leaving groups that L may represent are mentioned above. We prefer to use the iodide, toluenesulphonate or methanesulphonate derivative.

In processes (d), (e) and (f), the reaction will take place under standard conditions, for example by reacting the two compounds in an inert solvent under basic conditions at room temperature for a period of up to 12 hours. We have frequently found it desirable to treat the amine with NaH before reacting with the compound of formula (VIII) or (IX).

Suitable leaving groups L are mentioned above. We prefer that L represents halide, particularly bromide. The alkylation of process (i) will take place under similar conditions.

In process (g), the esterification reaction will take place under conditions known to persons skilled in the art. For example the carboxylic acid may be reacted with the appropriate alkyl alcohol under conditions of acid or base catalysis in a polar organic solvent at ambient or elevated temperature.

In processes (h) and (j), the hydrolysis will take place on treatment with acid and warming. In the case of hydrolysis of the cyano compound, the amide is produced with milder conditions and the carboxylic acid with more sever conditions. Suitable conditions for these reactions will be known to a person skilled in the art. Such cyano compounds may be prepared by processes which are described elsewhere here or are known per se.

In process (k), the reaction will take place under conditions well known for preparation of an amide. The corresponding amines are well known compounds. The corresponding acids may be prepared by analogy with methods disclosed here or in conjunction with methods well known in the art.

In process (l), the reaction will take place on mixing the reagents in an inert solvent at ambient or elevated temperature. The aryl hydroxide can be prepared by treating the aryl hydroxy compound with strong base (in protic solvents) or with an alkali metal (in non-protic solvents).

In process (m), the reaction will typically take place on refluxing the reaction mixture for up to 4 hours or until reaction is complete.

In process (n), the reaction will typically take place in a polar protic solvent such as ethanol in the presence of base at a temperature of between 0° C. and room temperature. We find it convenient to perform the reaction in a pressure bottle.

Salts of compounds of formula (I) may be formed by reacting the free acid, base or a salt, enantiomer, tautomer or protected derivative thereof, with one or more equivalents of the appropriate base or acid. The reaction may be carried out in a solvent or medium in which the salt is insoluble or in a solvent in which the salt is soluble, eg water, dioxan, ethanol, tetrahydrofuran or diethyl ether, or a mixture of solvents, which may be removed in vacuo or by freeze drying. The reaction may be a metathetic process or it may be carried out on an ion exchange resin.

Compounds of formula (VI) may be prepared by following the method of Rasmussen et al in *Synthesis,* 1988, 456–459. Compounds of formula (VI) can thus be prepared by reacting a compound of formula (II)

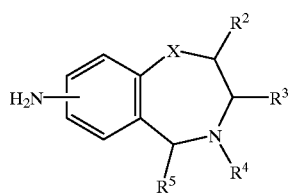

(II)

wherein X, $R^2$, $R^3$, $R^4$ and $R^5$ are as defined above, with benzoyl isothiocyanate in an organic solvent such as acetone optionally in the presence of acid (e.g. trifluoroacetic acid) followed by aqueous-alkaline cleavage of the resultant benzoylthiourea derivative. Compounds of formula (VI) may also be prepared by reacting a compound of formula (II) with sodium thiocyanate in water.

The compounds of formula (II) may be prepared by reduction of a corresponding compound of formula (X)

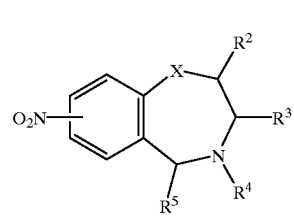

(X)

wherein X, $R^2$, $R^3$, $R^4$ and $R^5$ are as defined above.

The reduction reaction may be performed under a number of conditions, for example those described in J. March "Advanced Organic Chemistry" on pages 1103–1104. These include catalytic hydrogenation, use of Zn, Sn or Fe metal, $AlH_3$—$AlCl_3$, sulphides and others. We prefer to perform the reaction by hydrogenation at atmospheric pressure for 3 to 6 hours in the presence of a palladium and carbon catalyst.

Compounds of formula (X) in which X represents $NR^6$, S and O may be prepared by cyclising a compound of formula (XI)

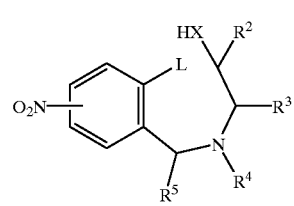

(XI)

wherein $R^2$, $R^3$, $R^4$, $R^5$ and X are as defined above and L is a leaving group.

Compounds of formula (XI) may be prepared by reaction of a compound of formula (XII)

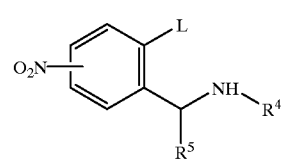

(XII)

wherein $R^4$, $R^5$ and L are as defined above with a compound of formula (XIII)

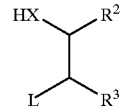

(XIII)

wherein X represents $NR^6$, S or O, $R^2$ and $R^3$ are as defined above and L is a leaving group.

Alternatively, compounds of formula (XI) may be prepared by reaction of a compound of formula (XIV)

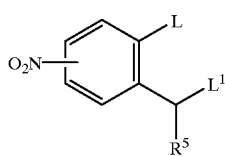

(XIV)

wherein $R^5$ and L are as defined above and $L^1$ is a leaving group, with a compound of formula (XV)

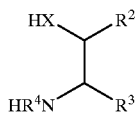

(XV)

wherein X represents $NR^6$, S or O and $R^2$, $R^3$ and $R^4$ are as defined above.

Compounds of formula (X) in which X represents $NR^6$, S and O may also be prepared by cyclising a compound of formula (XVI)

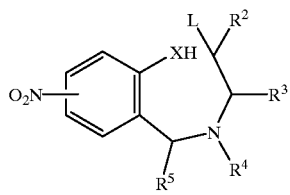

(XVI)

wherein $R^2$, $R^3$, $R^4$, $R^5$ and X are as defined above and L is a leaving group.

Compounds of formula (XVI) may be prepared by reaction of a compound of formula (XVII)

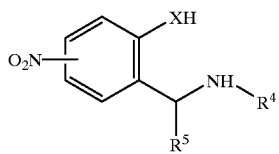

(XVII)

wherein $R^4$ and $R^5$ are as defined above and X represents $NR^6$, S or O, with a compound of formula (XVIII)

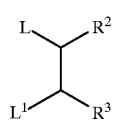

(XVIII)

wherein $R^2$ and $R^3$ are as defined above and L and $L^1$ are leaving groups.

Alternatively, compounds of formula (XVI) may be prepared by reaction of a compound of formula (XIX)

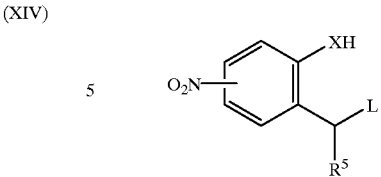

(XIX)

wherein X represents $NR^6$, S or O and L and $R^5$ are as defined above with a compound of formula (XX)

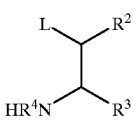

(XX)

wherein $R^2$, $R^3$ and $R^4$ are as defined above and L represents a leaving group.

The reactions of compounds of formula (XII) and (XIII), (XIV) and (XV), (XVII) and (XVIII) and (XIX) and (XX) may be performed under conditions well known to a person skilled in the art; typically on combining the ingredients in an inert solvent. Intermediate compounds of formula (XI) or (XVI) may not be isolated as the compound of formula (X) may be formed directly. Suitable leaving groups L and $L^1$ are mentioned above. The cyclisation reactions may also take place on removal of protecting groups. In the above reactions it may be desired to render the nucleophilic group —XH in compounds of formula (XI), (XII), (XV), (XVI), (XVII) and (XIX) more reactive by treatment with base.

Compounds of formula (X) may also be prepared by nitration of a compound of formula (XXI)

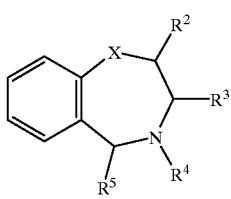

(XXI)

wherein X, $R^2$, $R^3$, $R^4$ and $R^5$ are as defined above.

The nitration reaction will take place under conditions well known to a person skilled in the art, e.g. on treatment with nitric acid and sulphuric acid or potassium nitrate and sulphuric acid in an inert organic solvent.

It may also be convenient to prepare compounds of formula (X) by nitration of a carbonyl or dicarbonyl derivative of a compound of formula (XXI); which nitrated carbonyl or dicarbonyl derivative may be reduced to the desired compound of formula (X) e.g. with diborane.

Compounds of formula (X) and (XXI), as well as certain carbonyl and dicarbonyl derivatives of compounds of formula (XXI) just mentioned may also be prepared by one of the numerous methods for preparation of bi- and tricyclic heterocyclic compounds.

For example a synthesis of compounds of formula (XXI) which is particularly preferred for compounds in which X represents a bond or $CH_2$ comprises the cyclisation of a compound of formula (XXII)

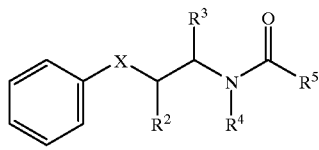

(XXII)

wherein X, $R^2$, $R^3$, $R^4$ and $R^5$ are as defined above.

This reaction may be performed following the conditions of Bischler-Napieralski described in J. March "Advanced Organic Chemistry" 3rd Edition, page 495 in which the amide is treated with $POCl_3$ or $PCl_5$ and heated. Alternatively the modification set out by Larsen et al in *J. Org. Chem.*, 1991, 56, 6034–6038 in which the amide is treated with oxalyl chloride followed by $FeCl_3$ and then acid may be preferred. Reduction of the corresponding imine or iminium salt, for example with sodium borohydride, provides the compound of formula (XXI).

Compounds of formula (XXII) may be prepared by reaction of a compound of formula (XXIII)

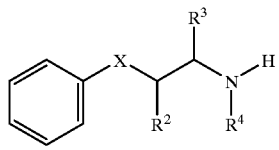

(XXIII)

wherein X, $R^2$, $R^3$ and $R^4$ are as defined above, with a compound of formula (XXIV)

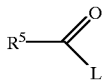

(XXIV)

wherein $R^5$ and L are as defined above under standard conditions for amide formation.

As a further modification of the Bischler-Napieralski reaction for the preparation of compounds of formula (I) in which $R^4$ and $R^5$ together represent a chain —$(CH_2)_m$— or —$(CH_2)_rY(CH_2)_p$—, such compounds may be prepared by cyclisation of a compound of formula (XXV)

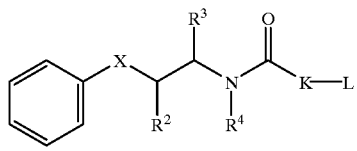

(XXV)

wherein X, $R^2$, $R^3$, $R^4$ and L are as defined above and K represents a chain —$(CH_2)_m$— or —$(CH_2)_rY(CH_2)_p$—.

The formation of both rings will typically take place on treatment with phosphoryl chloride and phosphorus pentoxide in an inert organic solvent at elevated temperature. This reaction, together with a more detailed description of reaction conditions, is described by Akaboshi et al in *Chem. Pharm. Bull.*, 1960, 8, 14–17.

Compounds of formula (XXV) may be prepared from simpler molecules by known methods.

An alternative synthesis for compounds of formula (XXI) in which $R^4$ and $R^5$ together represent a chain —$(CH_2)_m$— or —$(CH_2)_rY(CH_2)_p$— comprises cyclisation of an α-hydroxy lactam as described by Brewer et al in *J. Med. Chem.*, 1989, 32, 2058–2062. Thus compounds of formula (XXI) in which $R^4$ and $R^5$ together represent a chain —$(CH_2)_m$— or —$(CH_2)_rY(CH_2)_p$— may be prepared by cyclisation of a compound of formula (XXVI)

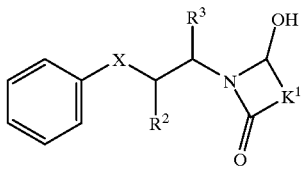

(XXVI)

wherein X, $R^2$ and $R^3$ are as defined above and $K^1$ represents a chain —$(CH_2)_{m-1}$— or —$(CH_2)_{r-1}Y(CH_2)_p$—. Cyclisation takes place on treatment with acid and produces a lactam which may be completely reduced with diborane to yield the corresponding compound of formula (XXI).

Compounds of formula (XXVI) may be prepared by reduction of the corresponding cyclic imide with sodium borohydride or sodium cyanoborohydride. The corresponding cyclic imide may readily be prepared from the corresponding primary amine and a dicarboxylic acid.

Further details of this synthesis may be obtained by reference to the above mentioned paper by Brewer et al.

A further synthesis for compounds of formula (XXI) in which $R^4$ and $R^5$ together represent a chain —$(CH_2)_m$— or —$(CH_2)_rY(CH_2)_p$— comprises reaction of a compound of formula (XXVII)

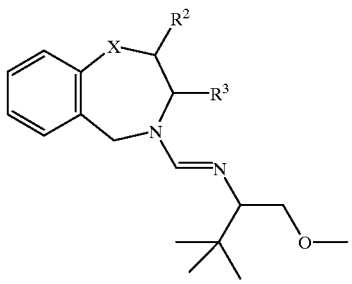

(XXVII)

wherein X $R^2$ and $R^3$ are as defined above, firstly with t-butyl lithium and then with a compound of formula (XXVIII)

Cl—K—I (XXVIII)

wherein K represents a chain —$(CH_2)_m$— or —$(CH_2)_rY(CH_2)_p$—, as described by Meyers and Hutchings in *Tetrahedron*, 1993, 49, 1807–1820.

A person skilled in the art would be able to envisage modification of the structures of compounds of formula (XXVII) and (XXVIII) as desired to achieve the same effect.

Compounds of formula (XXVII) may be prepared from simpler compounds which may be prepared according to the methods described here and as described in the Meyers and Hutchings paper.

Compounds of formula (XXI) in which $R^4$ represents hydrogen may also be prepared by reaction of a compound of formula (XXIX)

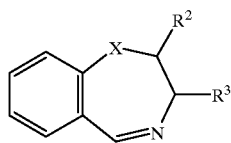

(XXIX)

wherein X, $R^2$ and $R^3$ are as defined above, with a carbon nucleophile.

Suitable carbon nucleophiles include cyanide, carboxylic acids capable of elimination of carbon dioxide (such as malonic acid), and alkynes. Others are described in J. March "Advanced Organic Chemistry" 3rd Edition on pages 306–7. Methods of modifying the functionality of group $R^5$ as desired will be well known to a person skilled in the art.

A typical reaction of this type is described by Böhme and Stöcker in *Arch. Pharmazie*, 1973, 306, 271–274.

Compounds of formula (XXIX) may be prepared by methods already described here, or by known methods.

Compounds of formula (XXI) in which X represents a bond or $CH_2$ and $R^3$ and $R^4$ together represent a chain $-(CH_2)_m-$ or $-(CH_2)_rY(CH_2)_p-$ may be prepared from a compound of formula (XXX)

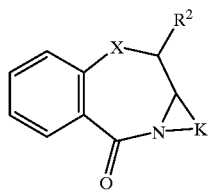

(XXX)

wherein $R^2$ is as defined above, X represents a bond or $CH_2$ and K represents a chain $-(CH_2)_m-$ or $-(CH_2)_rY(CH_2)_p-$ by reduction with diborane or by other known methods. Compounds of formula (XXI) in which $R^5$ represents hydrogen may be prepared by reduction of the corresponding compound of formula (XXX). Compounds of formula (XXI) in which $R^5$ does not represent hydrogen may be obtained via a process of nucleophilic addition onto the amide carbonyl of the compound of formula (XXX).

Compounds of formula (XXX) may be prepared following the method of Edwards and Meyers as set out in *Tetrahedron Lett.*, 1984, 25, 939–942. In this way, compounds of formula (XXX) may be prepared by reaction of a compound of formula (XXXI)

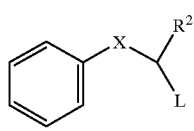

(XXXI)

wherein X represents a bond or $CH_2$, $R^2$ is as defined above and L is a leaving group, preferably halogen, with a compound of formula (XXXII)

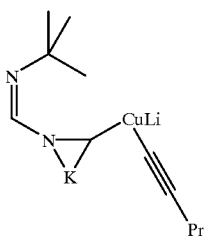

(XXXII)

wherein K represents a chain $-(CH_2)_m-$ or $-(CH_2)_rY(CH_2)_p-$.

Compounds of formula (XXXII) may be prepared following methods set out in the above mentioned Edwards and Meyers papers.

A person skilled in the art would be able to envisage modification of the structure of compounds of formula (XXXII) as desired to achieve the same effect.

Compounds of formula (XXI) in which $R^4$ and $R^5$ represent hydrogen may also be prepared by a synthesis based on ring expansion to convert a cyclic ketone into a cyclic amide as set out by Grunewald and Dahanukar in *J. Heterocyclic Chem.*, 1994, 31, 1609–1617.

Thus, a compound of formula (XXXIII)

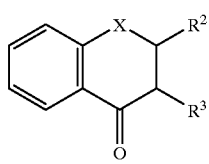

(XXXIII)

wherein X, $R^2$ and $R^3$ are as defined above may be converted to a compound of formula (XXXIV)

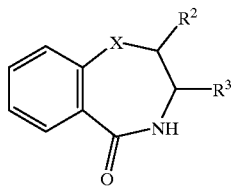

(XXXIV)

wherein X, $R^2$ and $R^3$ are as defined above on treatment with sodium azide in acid. Further details of the reaction conditions may be obtained by reference to the above mentioned Grunewald and Dahanukar paper.

Compounds of formula (XXXIV) may be converted to desired compounds of formula (I) by known methods.

It will be apparent to a person skilled in the art that the compounds of formula (XXII), (XXIII), (XXV), (XXVI), (XXVII), (XXIX), (XXX), (XXXI), (XXXIII) and (XXXIV) may desirably be prepared in nitrated form. Nitration may be achieved by treatment of the non-nitrated analogue with nitric acid and sulphuric acid or potassium nitrate and sulphuric acid under standard conditions.

Intermediate compounds may be prepared as such or in protected form. In particular amino groups and group XH when XH represents OH, SH or $NHR^6$ may be protected. Suitable protecting groups are described in the standard text "Protective Groups in Organic Synthesis", 2nd Edition (1991) by Greene and Wuts. Amine-protecting groups which may be mentioned include alkyloxycarbonyl C2 to 7, e.g t-butyloxycarbonyl, phenylalkyloxycarbonyl C8 to 13, benzyloxycarbonyl or trifluoroacetate. Deprotection will normally take place on treatment with aqueous base or aqueous acid.

Compounds of formula (X), (XI), (XII), (XV), (XVI), (XVII), (XX), (XXI), (XXII), (XXIII) and (XXV) in which $R^4$ represents alkyl C1 to 6, —$(CH_2)_cOH$, —$(CH_2)_cOAr$ or —$(CH_2)_nAr$ may also be prepared by alkylating or arylating the corresponding compound in which $R^4$ represents hydrogen following process (d) above.

Compounds of formula (IV) may be prepared by analogous processes to those described for the preparation of compounds of formula (II). Compounds of formula (IV) may be converted to corresponding compounds of formula (II) by treatment with a base. Compounds of formula (II) may be converted to corresponding compounds of formula (IV) by treatment with a protic acid HA, for example one of those listed above.

Compounds of formula (III) are either known or may be prepared by known methods. For example, compounds of formula (III) in which L represents thioalkyl may be prepared by treatment of the corresponding thioamide of formula (XXXV)

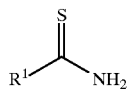

(XXXV)

wherein $R^1$ is as defined above, with an alkyliodide under conditions well known to a person skilled in the art.

Compounds of formula (V), (VIII), (IX), (XII), (XIII), (XIV), (XV), (XVII), (XVIII), (XIX), (XX), (XXIII), (XXIV), (XXVIII), (XXXI) (XXXIII) and (XXXV) are either known or may be prepared by conventional methods known per se.

It will be apparent to a person skilled in the art that it may be desirable to protect an amine or other reactive group in an intermediate compound using a protecting group as described in the standard text "Protective Groups in Organic Synthesis", 2nd Edition (1991) by Greene and Wuts. Suitable amine-protecting groups are mentioned above.

The compounds of the invention and intermediates may be isolated from their reaction mixtures by standard techniques.

The compounds of formula (I) may exist in tautomeric, enantiomeric or diasteroisomeric forms, all of which are included within the scope of the invention. The various optical isomers may be isolated by separation of a racemic mixture of the compounds using conventional techniques, e.g. fractional crystallisation, or HPLC. Alternatively the individual enantiomers may be made by reaction of the appropriate optically active starting materials under reaction conditions which will not cause racemisation.

Intermediate compounds may also exist in enantiomeric forms and may be used as purified enantiomers, diastereomers, racemates or mixtures.

As a further aspect of the invention we provide the new compounds of formulae (II), (VI) and (X).

The compounds of general formula (I) possess useful pharmacological activity in animals. Thus, they possess useful nitric oxide synthase inhibiting activity, and in particular, they exhibit good selectivity for inhibition of the neuronal isoform of nitric oxide synthase. They should thus be useful in the treatment or prophylaxis of human diseases or conditions in which the synthesis or oversynthesis of nitric oxide forms a contributory part. Examples of such diseases or conditions include hypoxia, such as in cases of cardiac arrest, stroke and neonatal hypoxia, neurodegenerative conditions including nerve degeneration and/or nerve necrosis in disorders such as ischaemia, hypoxia, hypoglycemia, epilepsy, and in external wounds (such as spinal cord and head injury), hyperbaric oxygen convulsions and toxicity, dementia, for example, pre-senile dementia, Alzheimer's disease and AIDS-related dementia, Sydenham's chorea, Parkinson's disease, Huntington's disease, Amyotrophic Lateral Sclerosis, Korsakoff's disease, imbecility relating to a cerebral vessel disorder, sleeping disorders, schizophrenia, anxiety, depression, seasonal affective disorder, jet-lag, depression or other symptoms associated with Premenstrual Syndrome (PMS), anxiety and septic shock. The compounds of formula (I), either alone or in combination with other analgesic agents such as opiates, are also useful in the treatment of pain, including neurogenic pain and neuropathic pain. Compounds of formula (I) may also be expected to show activity in the prevention and reversal of tolerance to opiates and diazepines, treatment of drug addiction and treatment of migraine and other vascular headaches. The compounds of the present invention may also show useful immunosuppressive activity, be useful in the treatment of prophylaxis of inflammation, in the treatment of gastrointestinal motility disorders, and in the induction of labour. The compounds may also be useful in the treatment of cancers that express nitric oxide synthase.

Compounds of formula (I) are expected to be particularly useful in the treatment of prophylaxis of hypoxia or stroke or ischaemia or neurodegenerative conditions or of migraine or for the prevention and reversal of tolerance to opiates and diazepines or for the treatment of drug addiction or for the treatment of pain and especially in the treatment or prophylaxis of hypoxia or stroke or ischaemia or neurodegenerative disorders or pain. We are particularly interested in conditions selected from the group consisting of hypoxia, ischaemia, stroke, pain and Amyotrophic Lateral Sclerosis.

Thus according to a further aspect of the invention we provide a compound of formula (I), or an optical isomer or racemate thereof or a pharmaceutically acceptable salt thereof, for use as a pharmaceutical.

According to another feature of the invention we provide the use of a compound of formula (I) or an optical isomer or racemate thereof or a pharmaceutically acceptable salt thereof, in the manufacture of a medicament for the treatment or prophylaxis of the aforementioned diseases or conditions; and a method of treatment or prophylaxis of one of the aforementioned diseases or conditions which comprises administering a therapeutically effective amount of a compound of formula (I), or an optical isomer or racemate thereof or a pharmaceutically acceptable salt thereof, to a person suffering from or susceptible to such a disease or condition.

For the above mentioned therapeutic indications, the dosage administered will, of course, vary with the compound employed, the mode of administration and the treatment desired. However, in general, satisfactory results are obtained when the compounds are administered to a human at a daily dosage of between 1 mg and 2000 mg (measured as the active ingredient) per day.

The compounds of formula (I), and optical isomers and racemates thereof and pharmaceutically acceptable salts thereof, may be used on their own, or in the form of appropriate medicinal formulations. Administration may be by, but is not limited to, enteral (including oral, sublingual or rectal), intranasal, topical or parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988.

According to the invention, there is provided a pharmaceutical formulation including preferably less than 80% by weight and more preferably less than 50% by weight of a compound of formula (I), or an optical isomer or racemate thereof or a pharmaceutically acceptable salt thereof, in admixture with as a pharmaceutically acceptable diluent or carrier.

We also provide a method of preparation of such a pharmaceutical formulation which comprises mixing the ingredients.

Examples of such diluents and carriers are: for tablets and dragees: lactose, starch, talc, stearic acid; for capsules: tartaric acid or lactose; for injectable solutions: water, alcohols, glycerin, vegetable oils; for suppositories: natural or hardened oils or waxes.

Compositions in a form suitable for oral, i.e. oesophageal administration include: tablets, capsules and dragees; sustained release compositions include those in which the active ingredient is bound to an ion exchange resin which is optionally coated with a diffusion barrier to modify the release properties of the resin.

The enzyme nitric oxide synthase has a number of isoforms and compounds of formula (I), and optical isomers and racemates thereof and pharmaceutically acceptable salts thereof, may be screened for neuronal nitric oxide synthase inhibiting activity by following procedures based on those of Bredt and Snyder in *Proc. Natl. Acad. Sci.,* 1990, 87, 682–685. Nitric oxide synthase converts $^3$H-L-arginine into $^3$H-L-citrulline which can be separated by cation exchange chromatography and quantified by scintillation counting.

Screen for Neuronal Nitric Oxide Synthase Inhibiting Activity

Enzyme was isolated from rat hippocampus or cerebellum. The cerebellum or hippocampus of a male Sprague-Dawley rat (250–275 g) is removed following $CO_2$ anaesthesia of the animal and decapitation. Cerebellar or hippocampal supernatant is prepared by homogenisation in 50 mM Tris-HCl with 1 mM EDTA buffer (pH 7.2 at 25° C.) and centifugation for 15 minutes at 20,000 g. Residual L-arginine is removed from the supernatant by chromatography through Dowex AG-50W-X8 sodium form and hydrogen form columns successively, and further centrifugation at 1000 g for 30 seconds.

For the assay, 25 $\mu$l of the final supernatant is added to each of 96 wells (of a 96 well filter plate) containing either 25 $\mu$l of an assay buffer (50 mM HEPES, 1 mM EDTA, 1.5 mM $CaCl_2$, pH 7.4) or 25 $\mu$l of test compound in the buffer at 22° C. and 25 $\mu$l of complete assay buffer (50 mM HEPES, 1 mM EDTA, 1.5 mM $CaCl_2$, 1 mM DTT, 100 $\mu$M NADPH, 10 $\mu$g/ml calmodulin, pH 7.4). Following a 10 minute equilibration period, 25 $\mu$l of an L-arginine solution (of concentration 18 $\mu$M $^1$H-L-arginine, 96 nM $^3$H-L-arginine) is added to each test tube to initiate the reaction. The reaction is stopped after 10 minutes by addition of 200 $\mu$l of a slurry of termination buffer (20 mM HEPES, 2 mM EDTA, pH 5.5) and Dowex AG-50W-X8 200–400 mesh.

Labelled L-citrulline is separated from labelled L-arginine by filtering each filter plate and 75 $\mu$l of each terminated reaction is added to 3 ml of scintillation cocktail. The L-citrulline is then quantified by scintillation counting.

In a typical experiment using the cerebellar supernatant, basal activity is increased by 20,000 dpm/ml of sample above a reagent blank which has an activity of 7,000 dpm/ml. A reference standard, N-nitro-L-arginine, which gives 80% inhibition of nitric oxide synthase at a concentration of 1 $\mu$M, is tested in the assay to verify the procedure.

In the screen for nitric oxide synthase inhibition activity, compound activity is expressed as $IC_{50}$ (the concentration of drug substance which gives 50% enzyme inhibition in the assay). $IC_{50}$ values for test compounds were initially estimated from the inhibiting activity of 1, 10 and 100 $\mu$M solutions of the compounds. Compounds that inhibited the enzyme by at least 50% at 10 $\mu$M were re-tested using more appropriate concentrations so that an $IC_{50}$ could be determined.

In the screen above, the compounds of Examples 1 to 12 below were tested and gave an $IC_{50}$ of less than 10 $\mu$M indicating that they are expected to show useful therapeutic activity.

When compared with other compounds, the compounds of formula (I), and optical isomers and racemates thereof and pharmaceutically acceptable salts thereof, have the advantage that they may be less toxic, be more efficacious, be longer acting, have a broader range of activity, be more potent, be more selective for the neuronal isoform of nitric oxide synthase enzyme, produce fewer side effects, be more easily absorbed or have other useful pharmacological properties.

The invention is illustrated by the following examples:

EXAMPLE 1

N-(3-Methyl-1,2,3,4-tetrahydroisoquinolin-7-yl)-2-thiophenecarboximidamide Dihydrochloride (a) 3-Methyl-7-nitro-3,4-dihydroisoquinoline 3-Methyl-3,4-dihydroisoquinoline (7.0 g, 48.2 mmol) was dissolved in concentrated sulfuric acid (150 ml) and to this was added potassium nitrate (4.9 g, 50.0 mmol). The mixture was allowed to stir overnight, dumped onto ice, and neutralized with the addition of concentrated ammonium hydroxide. The precipated solids were collected by filtration, washed, and air-dried: 7.5 g (82%), m.p. 110–2° C.

(b) 3-Methyl-7-nitro-1,2,3,4-tetrahydroisoquinoline Hydrochloride

To 3-methyl-7-nitro-3,4-dihydroisoquinoline (7.5 g, 39.4 mmol) in MeOH (150 ml) was added sodium borohydride (1.64 g, 43.4 mmol) portionwise. When the addition was complete, the mixture was evaporated, dumped into water and extracted with ethyl acetate (3×100 ml). The combined extracts were washed with water, dried over magnesium sulfate, filtered, and concentrated to an oil. The oil was dissolved in ethanol and treated with isopropanol-HCl. The solids were collected by filtration: 7.5 g (84%), m.p.>265° C. (dec.).

(c) 3-Methyl-7-amino-1,2,3,4-tetrahydroisoquinoline

3-Methyl-7-nitro-1,2,3,4-tetrahydroisoquinoline (3.0 g, 13.1 mmol) was dissolved in MeOH (100 ml) and hydrogenated at 50 psi in the presence of a catalytic quantity of 10% Pd—C. After 1 h the mixture was filtered through glass and evaporated to an oil which was used immediately in the next reaction.

(d) N-(3-Methyl-1,2,3,4-tetrahydroisoquinolin-7-yl)-2-thiophenecarboximidamide Dihydrochloride To 3-methyl-7-amino-1,2,3,4-tetrahydroisoquinoline (2.47 g, 11.7 mmol) in 1-methyl-2-pyrrolidinone (30 ml) was added S-methyl-2-thiophenethiocarboximide hydroiodide (see WO 95/05363, Example 1(d)) (3.90 g, 13.5 mmol).

The mixture was stirred for 24 h at 45° C., dumped into basic water and extracted with ethyl acetate (3×100 ml). The combined extracts were washed with water, dried over magnesium sulfate, filtered, and concentrated to a solid which was recrystallized from ethyl acetate-hexane. The solid was dissolved in ethanol and treated with isopropanol-HCl. The resulting salt was collected by filtration: 1.5 g (37%), m.p.>210° C. (dec.).

EXAMPLE 2

N-(3-Ethyl-1,2,3,4-tetrahydroisoquinoline-7-yl)-2-thiophenecarboximidamide Dihydrochloride (a) N-(1-Benzyl-propyl)-formamide To a stirred solution of formic acid (250 ml) and formamide (500 ml) was added 1-phenyl-2-butanone (25 g, 0.168 mols); the reaction was then heated to 165–170° C. for four hours. The reaction was then cooled and poured into water (1 l). The aqueous phase was then extracted with ethyl acetate (3×100 ml). The organic phase was washed with saturated sodium bicarbonate (2×200 ml) and dried over magnesium sulfate. Evaporation of the solvent yielded an oil (24.1 g, 80%).

The following steps follow a process analogous to that described by Larsen et al in *J. Org. Chem.*, 1991, 56, 6034–6038:

(b) 4-Ethyl-5,9b-dihydro-4H-1-oxa-3a-aza-cyclopental[a]naphthalene-2,3-dione

To a stirred solution of N-(benzyl-propyl)-formamide (23.8 g, 0.13 mols) in dichloromethane (1300 ml) was added (2.0M) oxalyl chloride (73.95 ml, 0.147 mols) over a ten minute period. The reaction was then stirred at room temperature for 30 min. At this time the reaction was cooled to −10° C. and $FeCl_3$ (26.0 g, 0.16 mols) was added all at once. The mixture was allowed to warm to room temperature and stirred for 18 h. Aqueous 2N HCl (1300 ml) was added and the reaction stirred 1 h, the layers separated, and the organic phase washed with brine (500 ml). Evaporation of the solvent yielded the title compound (29.4 g, 95%).

(c) 3-Ethyl-3,4-dihydroisoquinoline

To a stirred solution of 4-ethyl-5,9b-dihydro-4H-1-oxa-3a-aza-cyclopental[a]naphthalene-2,3-dione (29.4 g, 0.12 mols) in methanol (1140 ml) was added concentrated sulfuric acid (60 ml) slowly. The reaction was then refluxed for 2 h. The solvent was evaporated and to the residue was added water (100 ml) and ethyl acetate (500 ml). The layers were then separated and the organic phase was then extracted with 2N HCl (2×200 ml). The aqueous layers were combined and made basic with concentrated ammonium hydroxide. The product was then extracted into dichloromethane and dried over magnesium sulfate. Evaporation of the solvent yielded 20.5 g.

(d) 3-Ethyl-7-nitro-3,4-dihydroisoquinoline

To concentrated sulfuric acid (150 ml) at 0° C. was added 3-ethyl-3,4-dihydro-isoquinoline (20.1 g, 0.12 mols) and potassium nitrate (12.13 g, 0.12 mols). The reaction was allowed to warm to room temperature for 24 h. The reaction was poured onto ice (1.5 l) and then the aqueous phase was made basic with ammonium hydroxide. A solid crystallized and was collected by filtration to yield the title compound (22.3 g, 91%), m.p. 61–62° C.

(e) 3-Ethyl-1,2,3,4-tetrahydroisoquinolin-7-amine Dihydrochloride

To a pressure bottle charged with 3-ethyl-7-nitro-3,4-dihydroisoquinoline (3.6 g, 17 mmols) dissolved in methanol (100 ml) and saturated isopropanol-HCl (20 ml) was added 10% Pd—C (250 mg), and the reaction hydrogenated for 1 h. The catalyst was removed by filtration and the solvent evaporated to yield 3-ethyl-1,2,3,4-tetrahydroisoquinolin-7-amine dihydrochloride (4.3 g).

(f) N-(3-Ethyl-1,2,3,4-tetrahydroisoquinolin-7-yl)-2-thiophenecarboximidamide Dihydrochloride To a stirred solution of 3-ethyl-1,2,3,4-tetrahydroisoquinolin-7-amine dihydrochloride (4.3 g, 17 mmols) in N-methylpyrrolidinone (50 ml) was added pyridine (2.05 g, 26 mmols). To the reaction was added S-methyl-2-thiophenethiocarboximide hydroiodide and the mixture was then heated to 40° C. for 18 h. The reaction was then poured into 20% sodium hydroxide (300 ml). The aqueous phase was then extracted with ethyl acetate (3×100 ml), and dried over magnesium sulfate. Evaporation of the solvent yielded a crude oil (4.2 g). A dihydrochloride salt was made from ethyl acetate and saturated isopropanol-HCl. The product N-(3-ethyl-1,2,3,4-tetrahydroisoquinolin-7-yl)-2-thiophenecarboximidamide dihydrochloride salt was dried at 80° C. for 24 h to yield 4.09 g, m.p. 181–182° C.

EXAMPLE 3

N-(1,3,4,6,7,11b-Hexahydro-2H-benzo[a]quinolizin-10-yl)-2-thiophenecarboximidamide Dihydrochloride (a) 10-Amino-1,3,4,6,7,11b-hexahydro-2H-benzo[a]quinolizine To a solution of 1,3,4,7,-tetrahydro-2H-benzo[a]quinolizinium chloride (3.6 g, 16 mmol) (S. Akaboshi, T. Kutsuma, and K. Achiwa, *J. Pharm. Bull.*, 1960, 8, 14) in concentrated sulfuric acid (25 ml) at 0° C. was added potassium nitrate (2.20 g, 20 mmol). The reaction mixture was stirred overnight, then poured into ice water (300 ml). Platinum(IV) oxide (0.2 g) was added and the solution was hydrogenated on a Parr Hydrogenator at 50 psi for 24 h. The solution was filtered and the filtrate basified with concentrated ammonium hydroxide and extracted twice with dichloromethane. The dried ($MgSO_4$) organic phase was concentrated to give a red oil (2.4 g, 75%). Chromatography on silica gel gave the title compound as a dark red oil (1.86 g, 58%), MS 230 $(M+H)^+$, $^1H$ NMR ($CDCl_3$) 6.85 (d, 1H), 6.52 (d, 1H), 6.48 (dd, 1H), 3.3–3.7 (broad s, 2H), 2.8–3.1 (m, 4H), 2.1–2.7 (m, 3H), 1.2–2.0 (m, 6H).

(b) N-(1,3,4,6,7,11b-Hexahydro-2H-benzo[a]quinolizin-10-yl)-2-thiophenecarboximidamide Dihydrochloride A solution of 10-amino-1,3,4,6,7,11b-hexahydro-2H-benzo[a]quinolizine (0.463 g, 2.29 mmol), pyridine hydrochloride (0.33 g, 2.9 mmol) and S-methyl 2-thiophenethiocarboximide hydroiodide (0.92 g, 3.2 mmol) in N-methylpyrrolidinone (3.5 ml) was heated at 45° C. for 3 h. The reaction mixture was poured into water, treated with decolorizing carbon and the solution filtered. The filtrate was basified with dilute NaOH and extracted twice with ethyl acetate. The dried ($MgSO_4$) organic phases were concentrated to give an oil. Chromatography on silica gel, using 2% methanol in chloroform saturated with ammonia, gave the title compound as an oil (0.28 g, 35%). The sample was taken up in ethanol and isopropanol and acidified with hydrogen chloride in isopropanol. Ethyl acetate was added to induce precipitation. After stirring overnight, the product was collected, washed with isopropanol and ether to give the title compound as a white solid (225 mg, 25.5%), MS 312 $(M+H)^+$, $^1H$ NMR ($d_6$-DMSO) 11.6–12.1, 9.7–10.1, and 8.8–9.4 (broad m, 4H exchangeable with $D_2O$), 8.2 (d, 1H), 8.16 (d, 1H), 7.50 (broad s, 1H), 7.3–7.4 (m, 3H), 4.45 (broad t, 1H), 3.1–3.9 (m, 5H), 3.26 (broad d, 1H), 2.87 (broad d, 1H), 1.6–2.3 (m, 5H).

EXAMPLE 4

N-(1,2,3,5,6,10b-Hexahydropyrrolo[2,1-a]
isoquinolin-9yl)-2-thiophenecarboximidamide (a) 1,2,3,5,6,10b-Hexahydropyrrolo[2,1-a]isoquinolin-9-amine This compound was prepared as described for Example 3(a). From 2,3,5,6-tetrahydro-1H-pyrrolo[2,1-a]isoquinolinium chloride (6.28 g, 27.7 mmol) was isolated the title compound as an oil (2.60 g, 50%), MS 189 (M+H)$^+$, $^1$H NMR (CDCl$_3$) 6.88 (d, 1H), 6.47 (dd, 1H), 6.39 (d, 1H), 3.4–3.7 (broad s, 2H), 3.3–3.4 (t, 1H), 2.9–3.2 (m, 3H), 2.4–2.8 (m, 3H), 2.2–2.3 (m, 1H), 1.6–2.0 (m, 3H).

(b) N-(1,2,3,5,6,10b-Hexahydropyrrolo[2,1-a]isoquinolin-9-yl)-2-thiophenecarboximidamide This compound was prepared as described in Example 3(b). From 1,2,3,5,6,10b-hexahydropyrrolo[2,1-a]isoquinolin-9-amine (972 mg, 5.16 mmol) was isolated, after trituration with cold ethyl acetate (5 ml), the title compound as a yellow solid (520 mg, 34%), m.p. 193–6° C.

EXAMPLE 5

N-(4-Hydroxy-2,3,4,5-tetrahydro-1H-2-benzazepin-8-yl)-2-thiophenecarboximidamide Bisfumarate (a) 4-Hydroxy-2,3,4,5-tetrahydro-1H-2-benzazepin-8-amine Hydrochloride A suspension of 4-hydroxy-8-nitro-2,3,4,5-tetrahydro-1H-2-benzazepine hydrochloride (1.80 g, 7.36 mmol) (G. L. Grunewald and V. H. Dahanukar, *J. Heterocycl. Chem.*, 1994, 31, 1609) and 5% Pd—C (0.2 g) in ethanol (100 ml) was hydrogenated at 50 psi for 2 h. The catalyst was filtered off and the solvent was concentrated to give a solid. This solid was dissolved in hot ethanol (50 ml) and ether (200 ml) was added slowly. The solid was collected, washed with ether (100 ml) and air-dried to give the title compound as a yellow solid (1.44 g, 91%), m.p. 232.5–4° C.

(b) N-(4-Hydroxy-2,3,4,5-tetrahydro-1H-2-benzazepin-8-yl)-2-thiophenecarboximidamide Bisfumarate A solution of 4-hydroxy-2,3,4,5-tetrahydro-1H-2-benzazepin-8-amine hydrochloride (1.29 g, 6.00 mmol) and S-methyl-2-thiophenethiocarboximide hydroiodide (2.22 g, 7.80 mmol) in N-methylpyrrolidinone (6.0 ml) was heated at 45° C. for 16 h. The reaction mixture was poured into water (200 ml), treated with decolorizing carbon and filtered. The filtrate was basified with dilute NaOH and sodium chloride added, this was extracted 4 times with ethyl acetate. The dried (MgSO$_4$) organic phase was concentrated to give an oil. Chromatography on silica gel, using 10–20% methanol in chloroform saturated with ammonia, gave the title compound as a solid (1.43 g, 83%). This solid was dissolved in a solution of methanol and isopropanol and fumaric acid (1.0 g, 9.3 mmol) was added and the solution was heated for 0.5 h. After cooling, the solid was collected to give the title compound as a white solid (1.73 g, 55%), m.p. 195–6° C. (dec.).

EXAMPLE 6

N-(1-(2-Hydroxyethyl)-1,2,3,4-tetrahydroisoquinolin-7-yl)-2-thiophenecarboximidamide Dihydrochloride (a) 7-Nitro-1,2,3,4-tetrahydroisoquinolin-1-acetic Acid A suspension of 7-nitro-3,4-dihydroisoquinoline (10.0 g, 56.1 mmol) and malonic acid (11.7 g, 112 mmol) in acetic acid (55 ml) was heated at 120° C. for 0.5 h. Upon cooling, the solvent was concentrated to give a red oil which was taken up in aqueous ethanol (50 ml of 75%). After crystallization had occurred, the solvent was cooled to 0° C. and the product collected. The title compound was isolated as a tan solid (10.9 g, 81%), m.p. 264–5° C. (dec.).

(b) 1-(2-Hydroxyethyl)-7-nitro-1,2,3,4-tetrahydroisoquinoline Hydrochloride

To a suspension of 7-nitro-1,2,3,4-tetrahydroisoquinolin-1-acetic acid in anhydrous THF (20 ml) at 0° C. was added 1.0M borane in THF (25 ml). The reaction mixture was slowly warmed to ambient temperature and stirring was continued for 4 h. Since the reaction was not proceeding to completion, additional borane (10 ml) was added and the solution heated at reflux for 1 h. Upon cooling to ambient temperature, the reaction was quenched by the addition of methanol (1 ml) and 6M hydrochloric acid (5 ml). The solution was heated at reflux for 2 h to decompose any borate intermediates and the solvent concentrated at the rotoevaporator. The resulting oil was taken up in water, made basic with dilute NaOH, and extracted twice with dichloromethane. The dried (MgSO$_4$) organic extracts were concentrated to give a solid. This solid was dissolved in hot ethanol (75 ml) and hydrochloric acid in ethanol added to give an acidic solution. The product was isolated by filtration of the precipitate to give the title compound as a light yellow solid (2.28 g, 84%), m.p. 238–40° C.

(c) 1-(2-Hydroxyethyl)-1,2,3,4-tetrahydroisoquinoline-7-amine Hydrochloride

To a solution of 1-(2-hydroxyethyl)-7-nitro-1,2,3,4-tetrahydroisoquinoline hydrochloride (2.18 g, 8.43 mmol) in ethanol (100 ml) was added 10% Pd—C (0.4 g) and the solution hydrogenated on the Parr Hydrogenator for 2 h. The reaction mixture was filtered to remove the catalyst and the filtrate reduced to about ⅓ of the volume. The solution was warmed and ether (150 ml) was added. The precipitate was collected to give the title compound as a yellow solid (1.81 g, 94%), m.p. 199.5–200.5° C.

(d) N-(1-(2-Hydroxyethyl)-1,2,3,4-tetrahydroisoquinolin-7-yl)-2-thiophenecarboximidamide Dihydrochloride This compound was prepared as described in Example 3(b). From 1-(2-hydroxyethyl)-1,2,3,4-tetrahydroisoquinolin-7-amine hydrochloride (1.38 g, 6.03 mmol) was isolated the title compound, after salt formation in isopropanol with hydrogen chloride, (1.30 g, 58%), m.p. 234–6° C.

EXAMPLE 7

N-(1-Methoxycarbonylmethyl-1,2,3,4-tetrahydroisoquinolin-7-yl)-2-thiophenecarboximidamide (a) 7-Nitro-1,2,3,4-tetrahydroisoquinoline-1-acetic Acid Methyl Ester Hydrochloride To a suspension of 7-nitro-1,2,3,4-tetrahydroisoquinoline-1-acetic acid (2.75 g, 11.5 mmol) in methanol (25 ml) at 0° C. was added dropwise thionyl chloride (3.6 ml, 41 mmol). After addition was complete, the reaction mixture was heated at reflux for 0.33 h. After cooling slightly, ether (50 ml) was added and the reaction mixture was cooled to 0° C. The precipitate was collected to give the title compound as a light yellow solid (3.09 g, 93%), m.p. 211–2° C.

(b) 7-Amino-1,2,3,4-tetrahydroisoquinoline-1-acetic Acid Methyl Ester Hydrochloride To a solution of 7-nitro-1,2,3,4-tetrahydroisoquinoline-1-acetic acid methyl ester hydrochloride (3.08 g, 10.7 mmol) in a solution of methanol (170 ml) and saturated hydrogen chloride in isopropanol (12 ml) was added 10% Pd—C (0.5 g). The reaction mixture was hydrogenated on a Parr Hydrogenator for 2 h at 50 psi. After the catalyst was removed by filtration, the solvent was concentrated to about ⅕ the volume. Isopropanol (70 ml) was added and the precipitate was collected to afford the title compound as a pale yellow solid (3.10 g, 98%), m.p. 245–6° C. (dec.).

(c) N-(1-Methoxycarbonylmethyl-1,2,3,4-tetrahydroisoquinolin-7-yl)-2-thiophenecarboximidamide A suspension of 7-amino-1,2,3,4-tetrahydro-1-thiopheneacetic acid methyl ester dihydrochloride (1.62 g, 5.52 mmol), S-methyl-2-thiophenethiocarboximide hydroiodide (2.00 g, 7.01 mmol), and pyridine (0.48 ml, 6.0 mmol) in N-methylpyrrolidinone (6.0 ml) was heated at 45° C. for 4 h. The reaction mixture was poured into water, basified with potassium carbonate and extracted twice with ethyl acetate. The combined organic phases were extracted twice with dilute hydrochloric acid, basified with potassium carbonate, extracted twice with ethyl acetate, dried ($MgSO_4$) and concentrated to give an oil. Column chromatography on silica gel, using 5–10% methanol in chloroform saturated with ammonia, afforded the title compound as an oil (1.29 g) which solidified on standing. An analytical sample was obtained by recrystallization from ethyl acetate-hexanes, m.p. 136–7.5° C.

EXAMPLE 8

N-(1,2,3,4-Tetrahydroisoquinoline-1-acetic Acid-7-yl)-2-thiophenecarboximidamide Lithium Salt N-(1-Methoxycarbonylmethyl-1,2,3,4-tetrahydroisoquinolin-7-yl)-2-thiophenecarboximidamide (Example 7) (729 mg, 2.21 mmol) and lithium hydroxide (55 mg, 2.3 mmol) in a solution of THF (10 ml), methanol (5 ml) and water (3 ml) were heated at reflux for 2 h. The solvent was evaporated at the rotoevaporator to give a solid. Trituration with ethanol (20 ml) afforded, after filtration, the title compound as a white solid (449 mg, 63%), MS 314 (M+H)$^+$, $^1$H NMR (d$_6$-DMSO), 7.68 (d, 1H), 7.53 (d, 1H), 7.03 (t, 1H), 6.90 (d, 1H), 6.61 (s, 1H), 6.54 (d, 1H), 6.35 (broad s, 2H), 4.08 (broad m, 1H), 3.0–3.2 (m, 1H), 3.0–3.2 (m, 1H), 2.3–2.9 (m, 5H).

EXAMPLE 9

N-(1-Aminocarbonylmethyl-1,2,3,4-tetrahydroisoquinolin-7-yl)-2-thiophenecarboximidamide Dihydrochloride (a) 7-Nitro-1,2,3,4-tetrahydroisoquinolin-1-acetonitrile A suspension of 7-nitro-3,4-dihydroisoquinoline (13.4 g, 76.1 mmol) and cyanoacetic acid (12.5 g, 150 mmol) in acetic acid (55 ml) was heated at reflux for 0.5 h. After evolution of carbon dioxide had ceased and the reaction mixture had cooled, the solvent was removed on the rotoevaporator. The residue was triturated with isopropanol (100 ml) and the solid was collected. The crude product was partitioned between ethyl acetate and dilute potassium carbonate solution. The dried ($MgSO_4$) organic phase was concentrated to give the title compound as an orange solid (12.6 g, 76%), MS 218 (M+H)$^+$. $^1$H NMR (CDCl$_3$) 8.03 (dd, 1H), 7.99 (d, 1H), 7.31 (d, 1H), 4.45 (t, 1H), 3.1–3.4 (m, 3H), 2.9–3.0 (m, 3H), 2.07 (broad s, 1H).

(b) 7-Nitro-1,2,3,4-tetrahydroisoquinoline-1-acetamide

To cold concentrated sulfuric acid (100 ml) was added, in a single portion, 7-nitro-1,2,3,4-tetrahydroisoquinoline-1-acetonitrile (12.6 g, 58.0 mmol). The reaction mixture was stirred for 6 h at that temperature after which time all the starting material had dissolved. The reaction mixture was poured on ice and the solution made basic with concentrated ammonium hydroxide at such a rate as to control the exotherm. The precipitated product was collected, washed with copious amounts of water, and air-dried to give the title compound as a red solid (12.1 g, 89%), m.p. 246–7° C. (dec.).

(c) 7-Amino-1,2,3,4-tetrahydroisoquinoline-1-acetamide Dihydrochloride

This compound was prepared as described for Example 2(e) except ethanol was used as the solvent. From 7-nitro-1,2,3,4-tetrahydroisoquinoline-1-acetamide (1.20 g) was isolated the title compound as an off-white solid (1.05 g, 85%), m.p. 168–70° C.

(d) N-(1-Aminocarbonylmethyl-1,2,3,4-tetrahydroisoquinolin-7-yl)-2-thiophenecarboximidamide Dihydrochloride This compound was prepared as described for Example 5(b). From 7-amino-1,2,3,4-tetrahydroisoquinoline-1-acetamide dihydrochloride (1.05 g, 3.58 mmol) was isolated the title compound as the free base (0.66 g, 58%). The dihydrochloride salt was prepared by dissolving the free base in isopropanol and adding hydrogen chloride in isopropanol until the solution was acidic, MS 315 (M+H)$^+$, $^1$H NMR (d$_6$-DMSO) 11.7–11.8 (broad s, 1H), 10.1–10.2 (broad s, 1H), 9.7–10.1 (broad s, 1H), 9.4–9.6 (broad s, 1H), 8.8–9.3 (broad s, 1H), 8.1–8.2 (m, 2H), 7.83 (broad s, 1H), 7.3–7.4 (m, 4H), 4.80 (broad m, 1H), 3.0–3.5 (m, 5H).

EXAMPLE 10

N-(2,3-Dimethyl-1,2,3,4-tetrahydroisoquinolin-7-yl)-2-thiophenecarboximidamide (a) 2,3-Dimethyl-7-nitro-1,2,3,4-tetrahydroisoquinoline Hydrochloride To 3-methyl-7-nitro-1,2,3,4-tetrahydroisoquinoline hydrochloride (2.0 g, 8.75 mmol) in 37% formaldehyde (7.0 ml, 87.5 mmol) was added 96% formic acid (3.5 ml, 87.5 mmol) and sodium formate (0.60 g, 8.75 mmol). The mixture was heated at reflux for 1 h, cooled, dumped into basic water and extracted with ethyl acetate (3×50 ml). The combined extracts were washed with water, dried over magnesium sulfate, filtered, and concentrated to an oil. The oil was dissolved in ethanol and treated with isopropanol-HCl. The solids were collected by filtration (2.0 g, 95%), m.p. 242–244° C.

(b) 2,3-Dimethyl-7-amino-1,2,3,4-tetrahydroisoquinoline Hydrochloride

To 2,3-dimethyl-7-nitro-1,2,3,4-tetrahydroisoquinoline hydrochloride (2.0 g, 8.24 mmol) in methanol (100 ml) was added a catalytic amount of 10% Pd—C. The mixture was hydrogenated at 50 psi for 1 h, filtered, and concentrated to a solid which was used immediately in the next reaction (1.6 g, 92%), m.p. 215–217° C.

(c) N-(2,3-Dimethyl-1,2,3,4-tetrahydroisoquinolin-7-yl)-2-thiophenecarboximidamide To 2,3-dimethyl-7-amino-1,2,3,4-tetrahydroisoquinoline hydrochloride (1.6 g, 7.60 mmol) in 1-methyl-2-pyrrolidinone (10 ml) was added S-methyl-2-thiophenethiocarboximide hydroiodide (2.5 g, 8.74 mmol). The mixture was stirred for 24 h at 45° C., dumped into basic water and extracted with ethyl acetate (3×50 ml). The combined extracts were washed with water, dried over magnesium sulfate, filtered, and concentrated to a oil which was purified by RPHPLC (acetonitrile-water, 0–60%; 50 min). Lyophilization afforded a white solid (1.45 g); MS (M+H)$^+$ 286.

EXAMPLE 11

(−)-N-(10-Methyl-2,3,5,10,11,11a-hexahydro-1H-pyrrolo[2,1-c][1,4]benzodiazapin-7-yl)-2-thiophenethiocarboximide Dihydrochloride (a) 10-Methyl-2,3-dihydro-1H-pyrrolo[2,1-c][1,4]benzodiazapine-5,11(10H,11aH)-dione To (S)-(+)-2,3-dihydro-1H-pyrrolo[2,1-c][1,4]benzodiazapine-5,11(10H,11aH)-dione (9.9 g, 45.8 mmol) in DMF (150 ml) at 0° C. was added NaH (2.0 g, 50.4 mmol). The mixture was warmed to room temperature and stirred for 1 h before methyl iodide (8.56 ml, 137 mmol) was added dropwise, After stirring for an additional 1 h, the mixture was dumped into water (1 l) and extracted with ethyl acetate (3×100 ml). The combined extracts were washed with water, dried over magnesium sulfate, filtered, and concentrated to a solid which was recrystallized from ethyl acetate-hexane (5.7 g, 54%), m.p. 118–120° C.

(b) 10-Methyl-7-nitro-2,3-dihydro-1H-pyrrolo[2,1-c][1,4]benzodiazapine-5,11(10H,11aH)-dione To 10-methyl-2,3-dihydro-1H-pyrrolo[2,1-c][1,4]benzodiazapine-5,11(10H,11aH)-dione (5.7 g, 24.7 mmol) in concentrated sulfuric acid (60 ml) at 0° C. was added potassium nitrate (2.62 g, 25.9 mmol). After stirring for 2 h the mixture was dumped onto ice (500 g) and extracted with ethyl acetate (5×75 ml). The combined extracts were washed with water, dried over magnesium sulfate, filtered, and concentrated to a solid which was recrystallized from ethyl acetate-hexane (5.2 g, 77%), m.p. 160–162° C.

(c) 10-Methyl-7-nitro-2,3,5,10,11,11a-hexahydro-1H-pyrrolo[2,1-c][1,4]benzodiazapine Hydrochloride To 10-methyl-7-nitro-2,3-dihydro-1H-pyrrolo[2,1-c][1,4]benzodiazapine-5,11(10H,11aH)-dione (5.2 g, 18.9 mmol) in THF (30 ml) was added 1.0M borane in THF (151 ml, 151 mmol). The mixture was brought to reflux for 6 h, cooled, quenched with 4N HCl (30 ml) and brought to reflux for an additional 1 h. The THF was evaporated and the aqueous layer made basic by the addition of 50% NaOH. The aqueous layer was extracted with ethyl acetate (5×75 ml) and the combined extracts were washed with water, dried over magnesium sulfate, filtered, and concentrated to a oil. The oil was dissolved in ethanol and treated with isopropanol-HCl. The solids were collected by filtration (2.6 g, 50%), m.p. 230–238° C.

(d) 7-Amino-10-methyl-2,3,5,10,11,11a-hexahydro-1H-pyrrolo[2,1-c][1,4]benzodiazapine Hydrochloride To 10-methyl-7-nitro-2,3,5,10,11,11a-hexahydro-1H-pyrrolo[2,1-c][1,4]benzodiazapine hydrochloride (2.6 g, 9.16 mmol) in methanol (100 ml) was added a catalytic amount of 10% Pd—C. The mixture was hydrogenated at 50 psi for 1 h, filtered, and concentrated to an oil which was used immediately in the next reaction.

(e) (−)-N-(10-Methyl-2,3,5,10,11,11a-hexahydro-1H-pyrrolo[2,1-c][1,4]benzodiazapin-7-yl)-2-thiophenecarboximidamide Dihydrochloride To 10-methyl-2,3,5,10,11,11a-hexahydro-1H-pyrrolo[2,1-c][1,4]benzodiazapin-7-amine hydrochloride (1.6 g, 7.60 mmol) in 1-methyl-2-pyrrolidinone (10 ml) was added S-methyl-2-thiophenethiocarboximide hydroiodide (2.5 g, 8.74 mmol). The mixture was stirred for 24 h at 45° C., dumped into basic water and extracted with ethyl acetate (3×50 ml). The combined extracts were washed with water, dried over magnesium sulfate, filtered, and concentrated to a solid which was recrystallized from ethyl acetate-hexane. The solid was dissolved in ethanol and treated with isopropanol-HCl. The salt was collected by filtration (1.2 g, 32%), m.p.>200° C. (dec.), [α]$_D$−84.15° (c 0.9899, MeOH).

EXAMPLE 12

N-(3-Propyl-1,2,3,4-tetrahydroisoquinolin-7-yl)-2-thiophenecarboximidamide Dihydrochloride To a stirred solution of 3-propyl-1,2,3,4-tetrahydroisoquinolin-7-amine dihydrochloride (3.0 g, 11 mmols) (prepared following a method analogous to that set out in Examples 1 and 2 for preparation of the methyl and ethyl analogues) in N-methylpyrrolidinone (50 ml) was added pyridine (1.0 ml, 12 mmols). To the reaction was added S-methyl-2-thiophenethiocarboximide hydroiodide (3.7 g, 13 mmol) and the mixture was then heated to 40° C. for 18 h. The reaction was then poured into 20% sodium hydroxide (300 ml). The aqueous phase was then extracted with ethyl acetate (3×100 ml), and dried over magnesium sulfate. Evaporation of the solvent yielded a crude oil. A salt was made from ethyl acetate, ethanol and saturated isopropanol-HCl. The product, N-(3-propyl-1,2,3,4-tetrahydroisoquinolin-7-yl)-2-thiophenecarboximidamide dihydrochloride was dried at 80° C. for 24 h, (2.9 g), m.p. 205–206° C.

EXAMPLE 13

(+)-N-(3-Ethyl-1,2,3,4-tetrahydroisoquinolin-7-yl)-2-thiophenecarboximidamide Dihydrochloride (a) (S) and (R)-3-Ethyl-7-nitro-1,2,3,4-tetrahydroisoquinoline To a solution of 3-ethyl-7-nitro-3,4-dihydroisoquinoline (15.8 g, Example 2 (d)) in methanol (100 ml) at 0° C. was added sodium borohydride (4g). After foaming had stopped, the reaction was poured into water (750 ml) and then the aqueous phase was extracted with ethyl acetate (3×300 ml). Evaporation gave 3-ethyl-7-nitro-1,2,3,4-tetrahydroisoquinoline as a tan oil (15.8 g).

The isomers were separated by selective crystallization as follows:

To a stirred solution of 3-ethyl-7-nitro-1,2,3,4-tetrahydroisoquinoline (15.8 g, 76 mmols) in ethanol (100 ml) was added dibenzoyl-L-tartaric acid (27.45 g, 76 mmol) dissolved in ethanol (100 ml). To this was added ether (150 ml), whereupon on standing a solid crystallized. This material was collected and dried (20.6 g). The above solid was recrystallized from refluxing methanol (2 l). This material (6.0 g) was 99.5% one isomer by capillary electrophoresis. The above compound was the dissolved in water (500 ml) and the aqueous phase then made basic and the compound extracted into ethyl acetate (3×200 ml). This yielded 3.5 g of material.

(b) (+)-3-Ethyl-1,2,3,4-tetrahydroisoquinolin-7-amine Dihydrochloride

To a pressure bottle charged with (+)-3-ethyl-7-nitro-1,2,3,4-tetrahydroisoquinoline (3.5 g) dissolved in methanol (100 ml) and saturated isopropanol-HCl (20 ml) was added 10% Pd—C (250 mg), and the reaction was hydrogenated for 1 h. The catalyst was removed by filtration and the solvent evaporated to give (+)-3-ethyl-1,2,3,4-tetrahydroisoquinolin-7-amine dihydrochloride (3.4 g), m.p. 199–200° C., [α]$_D$+68.4° (c 0.976, methanol).

(c) (+)-N-(3-Ethyl-1,2,3,4-tetrahydroisoquinolin-7-yl)-2-thiophenecarboximidamide Dihydrochloride To a stirred solution of (+)-3-ethyl-1,2,3,4-tetrahydroisoquinolin-7-amine dihydrochloride (3.0 g, 12 mmols) in N-methylpyrrolidinone (50 ml) was added pyridine (1.4 ml, 18 mmols). To the reaction was added S-methyl-2-thiophenethiocarboximide hydroiodide (4.1 g, 14 mmol) and the mixture was then heated to 40° C. for 18 h. The reaction was then poured into 20% sodium hydroxide (300 ml). The aqueous phase was then extracted with ethyl acetate (3×100 ml), and dried over magnesium sulfate. Evaporation of the solvent yielded a crude oil. A dihydrochloride salt was made from ethanol and ether and saturated ethanol-HCl. (+)-N-(3-Ethyl-1,2,3,4-tetrahydroisoquinolin-7-yl)-2-thiophenecarboximidamide dihydrochloride (0.9 g), m.p. 187–188° C., [α]$_D$+52.8° (c 0.996, methanol).

EXAMPLE 14

(−)-N-(3-Ethyl-1,2,3,4-tetrahydroisoquinolin-7-yl)-2-thiophenecarboximidamide Dihydrochloride This compound was prepared following a method analogous to that of Example 13.

(a) (−)-3-Ethyl-1,2,3,4-tetrahydroisoquinolin-7-amine Dihydrochloride

The above compound had a rotation of $[\alpha]_D$ −69.29° (c 1.104, methanol), m.p. 201–202° C.

(b) (−)-N-(3-Ethyl-1,2,3,4-tetrahydroisoquinolin-7-yl)-2-thiophenecarboximidamide Dihydrochloride The above compound had a rotation of $[\alpha]_D$ −57.6° (c 1.156, methanol), m.p. 193–194° C.

EXAMPLE 15

N-(3-Ethyl-2-methyl-1,2,3,4-tetrahydroisoquinolin-7-yl)-2-thiophenecarboximidamide (a) 3-Ethyl-7-nitro-1,2,3,4-tetrahydroisoquinoline To a stirred solution of 3-ethyl-7-nitro-3,4-dihydroisoquinoline (5.0 g) in methanol (100 ml) was added sodium borohydride (3×0.4 g), and the reaction was stirred for 2 h. Enough 4N HCl was added to the reaction mixture to make it acidic whereupon a solid crystallized out and was collected by filtration (4.0 g).

(b) 3-Ethyl-2-methyl-7-nitro-1,2,3,4-tetrahydroisoquinoline Hydrochloride

To a stirred solution of 3-ethyl-7-nitro-1,2,3,4-tetrahydroisoquinoline hydrochloride (4.0 g, 8 mmol) in formaldehyde (15 ml) was added formic acid (7.0 ml) and the reaction was then refluxed for 1.5 h. The reaction was cooled and poured into water (300 ml) and made basic with 50% NaOH. The aqueous phase was then extracted with dichloromethane (3×100 ml), and the organic phase dried over MgSO₄. Evaporation of the solvent yielded a crude oil. A hydrochloride salt was made from ethanol-HCl, (1.8 g), m.p. 240–241° C.

(c) 7-Amino-3-ethyl-2-methyl-1,2,3,4-tetrahydroisoquinoline Dihydrochloride

To a pressure bottle charged with 3-ethyl-2-methyl-7-nitro-1,2,3,4-tetrahydroisoquinoline hydrochloride (3.6 g, 17 mmols) dissolved in methanol (100 ml) and saturated isopropanol-HCl (20 ml) was added 10% Pd—C (250 mg), and the reaction was hydrogenated for 1 h. The catalyst was removed by filtration and the solvent evaporated to give the title compound (4.3 g).

(d) N-(3-Ethyl-2-methyl-1,2,3,4-tetrahydroisoquinolin-7-yl)-2-thiophenecarboximidamide To a stirred solution of 7-amino-3-ethyl-2-methyl-1,2,3,4-tetrahydroisoquinoline dihydrochloride (1.7 g, 7.1 mmols) in N-methylpyrrolidinone (50 ml) was added pyridine (0.5 g, 7.1 mmols). To the reaction was added S-methyl-2-thiophenethiocarboximide hydroiodide (2.2 g, 7.8 mmol) and the mixture was then heated to 40° C. for 18 h. The reaction was then poured into 20% sodium hydroxide (300 ml). The aqueous phase was then extracted with ethyl acetate (3×100 ml), and the extracts were dried over magnesium sulfate. Evaporation of the solvent yielded N-(3-ethyl-2-methyl-1,2,3,4-tetrahydroisoquinolin-7-yl)-2-thiophenecarboximidamide (600 mg), m.p. 125–126° C.

EXAMPLE 16

N-(1,3,4,6,11,11a-Hexahydro-2H-benzo[b]quinolizin-8-yl)-2-thiophenecarboximidamide Dihydrochloride (a) 1,3,4,6,11,11a-Hexahydro-2H-benzo[b]quinolizin-6-one To a solution of 1,3,4,6-tetrahydro-2H-benzo[b]quinolizin-6-one (4.02 g, 20.2 mmol) (M. A. Haimova, V. I. Ognyanov, and N. M. Mollov, *Synthesis,* 1980, 845) in ethanol (250 ml) and 2.5M hydrochloric acid (10 ml) was added 10% palladium-on-carbon (0.8 g) and the solution was shaken on a Parr Hydrogenator for 72 h. The catalyst was filtered off and the filtrate was concentrated to give an oil which was partitioned between ethyl acetate and dilute base. The dried (magnesium sulfate) organic phase was concentrated in vacuo and then placed on a high vacuum system to give the title compound as a white solid (3.8 g, 94%), m.p. 88–92° C.

(b) 8-Nitro-1,3,4,6,11,11a-hexahydro-2H-benzo[b]quinolizin-6-one 1,3,4,6,11,11a-Hexahydro-2H-benzo[b]quinolizin-6-one (3.78 g, 18.7 mmol) was dissolved in concentrated sulfuric acid (50 ml) at 0° C., potassium nitrate (2.02 g, 20 mmol) was added and the reaction mixture was stirred overnight. The reaction mixture was poured onto ice (200 g) and was partially neutralized with concentrated ammonium hydroxide. The precipitate was collected and air-dried to give the title compound as a yellow solid (4.22 g, 92%), m.p. 137–42° C.

(c) 8-Nitro-1,3,4,6,11,11a-hexahydro-2H-benzo[b]quinolizine Hydrochloride

To a solution of 8-nitro-1,3,4,6,11,11a-hexahydro-2H-benzo[b]quinolizin-6-one (4.18 g, 17.0 mmol) in anhydrous THF (50 ml) was added 1.0M borane i THF (50 ml). The reaction mixture was heated at reflux for 18 h. After cooling to room temperature, the excess borane was quenched by the addition of methanol and 6M hydrochloric acid (6 ml) and the solution was heated for 2 h. The solvent was removed in vacuo and the residue was taken up in water. The resulting solution was basified with sodium hydroxide and extracted twice with dichloromethane. The dried (magnesium sulfate) organic phase was concentrated to give an oil which was immediately taken up in ethanol (60 ml). Hydrochloric acid in ethanol was added until the solution was distinctly acidic and the solution was stirred for several hours at ambient temperature. The precipitate was collected, washed with ethanol, and air-dried to give the title compound as a white solid (3.03 g, 70%), m.p. 245–7° C. (dec.).

(d) 1,3,4,6,11,11a-Hexahydro-2H-benzo[b]quinolizin-8-amine Hydrochloride

8-Nitro-1,3,4,6,11,11a-hexahydro-2H-benzo[b]quinolizine hydrochloride (2.93 g, 10.9 mmol) was dissolved in ethanol (150 ml) and 10% palladium-on-carbon (0.4 g) was added and the solution was shaken on a Parr Hydrogenator for 2 h. The catalyst was filtered off and the catalyst was washed with water. The filtrate was concentrated and absolute ethanol was added and evaporated to drive off excess water. The resulting solid was taken up in hot ethanol (75 ml) and ether (100 ml) was added slowly. The precipitate which formed was collected and dried in the air to give the title compound as an off-white solid (2.48 g, 95%), m.p. 241–3° C. (dec.).

(e) N-(1,3,4,6,11,11a-Hexahydro-2H-benzo[b]quinolizin-8-yl)-2-thiophenecarboximidamide Dihydrochloride This compound was prepared by analogy with the method of Example 5 (b); from 1,3,4,6,7,11a-hexahydro-2H-benzo[b]quinolizin-8-amine hydrochloride (1.10 g, 4.61 mmol) was isolated after recrystallization from ethyl acetate-hexanes the free base (0.78 g). This was immediately taken up in isopropanol and acidified with hydrochloric acid in isopropanol. The title compound was precipitated by the addition of ethyl acetate to give an off-white solid (0.96 g, 54%), MS 312 (M+H)$^+$; NMR (d$_6$-DMSO) 11.7–12.0 (broad s, 2H), 9.7–10.2 (broad s, 1H), 9.0–9.5 (broad s, 1H), 8.22 (d, 1H), 8.16 (d, 1H), 7.3–7.4 (m, 3H), 7.27 (s, 1H), 4.44 (d, J=17, 1H), 4.24 (dd, J=7, 17, 1H), 3.4–3.6 (m, 2H), 3.0–3.2 (m, 3H), 1.5–2.2 (m, 6H).

EXAMPLE 17

N-(5,7,8,9,10,11,11a,12-Octahydroazepino[1,2-b] isoquinolin-3-yl)-2-thiophenecarboximidamide Dihydrochloride (a) 8,9,10,11-Tetrahydro-7H-azepino[1,2-b]isoquinolin-5-one Homophthalic anhydride (4.86 g, 30 mmol) was added portionwise over 10 minutes to a refluxing solution of 1-aza-2-methoxycycloheptene (4.20 g, 33 mmol) in toluene. After addition was complete, the reaction mixture was heated an additional 1 h before cooling to ambient temperature. The reaction mixture was diluted with chloroform, the resulting solution was washed twice with sodium hydroxide, and the dried (magnesium sulfate) organic layer was concentrated in vacuo. The residue was chromatographed on silica gel using chloroform, followed by 4% methanol in chloroform, as eluent to give the desired compound. This was triturated with 20% ether in hexanes (40 ml) to yield the title compound as an off-white solid (2.21 g, 42%), m.p. 99–101° C.

(b) 8,9,10,11,11a,12-Hexahydro-7H-azepino[1,2-b] isoquinolin-5-one

This compound was prepared by analogy with the method of Example 16 (a); from 8,9,10,11-tetrahydro-7H-azepino [1,2-b]isoquinolin-5-one (2.60 g) was isolated the title compound as a crude, colorless oil (2.53 g), MS 216 (M+H)$^+$, which was carried on without purification to the next step.

(c) 3-Nitro-8,9,10,11,11a,12-hexahydro-7H-azepino[1,2-b] isoquinolin-5-one

To a solution of 8,9,10,11,11a,12-hexahydro-7H-azepino [1,2-b]isoquinolin-5-one (2.50 g, 11.6 mmol) in concentrated sulfuric acid (30 ml) at 0° C. was added in a single portion potassium nitrate (1.23 g, 12.2 mmol). After the reaction mixture had stirred overnight, it was poured onto ice and basified with concentrated ammonium hydroxide. The aqueous phase was extracted twice with dichloromethane, dried (magnesium sulfate), and concentrated to leave about 15 ml of solvent. Hexanes (100 ml) was added and the solution was placed in the freezer. The precipitated product was collected and dried to give the title compound as a yellow solid (1.94 g, 64%), m.p. 117.5–9° C.

(d) 3-Nitro-5,7,8,9,10,11,11a,12-octahydroazepino[1,2-b] isoquinolin Hydrochloride This compound was prepared by analogy with the method of Example 16 (c); from 3-nitro-8,9,10,11,11a,12-hexahydro-7H-azepino[1,2-b]isoquinolin-5-one (1.90 g, 7.30 mmol) was isolated the title compound as a white solid (1.92 g, 93%), m.p. 253–5° C. (dec.).

(e) 5,7,8,9,10,11,11a,12-Octahydroazepino[1,2-b] isoquinolin-3-amine Hydrochloride This compound was prepared by analogy with the method of Example 16 (d); from 3-nitro-5,7,8,9,10,11,11a,12-octahydroazepino[1,2-b]isoquinolin hydrochloride (1.90 g, 6.72 mmol) was isolated the title compound as an off-white solid (1.64 g, 96%), m.p.>230° C. (dec.).

(f) N-(5,7,8,9,10,11,11a,12-Octahydroazepino[1,2-b] isoquinolin-3-yl)-2-thiophenecarboximidamide Dihydrochloride This compound was prepared by analogy with the method of Example 5 (b); from 5,7,8,9,10,11,11a, 12-octahydroazepino[1,2,-b]isoquinolin-3-amine hydrochloride (1.50 g, 5.73 mmol) was isolated 1.19 g (62%) of the free base form of the title compound, m.p. 127–8.5° C. The dihydrochloride salt was prepared by dissolving the free base in isopropanol and acidifying with hydrochloric acid in ethanol. The salt was precipitated by the addition of ethyl acetate, MS 326 (M+H)$^+$; NMR (d$_6$-DMSO) 10.1–10.3 (broad, 1H), 9.9–10.1 (broad, 1H), 9.1–9.3 (broad, 1H), 8.21 (d, 1H), 8.16 (d, 1H), 7.3–7.4 (m, 3H), 7.27 (s, 1H), 4.4–4.6 (broad m, 2H), 3.3–3.6 (m, 4H), 3.05 (d, 1H), 1.5–2.3 (m, 8H).

EXAMPLE 18

N-(2-(2-Hydroxyethyl)-1,2,3,4-tetrahydroisoquinolin-7-yl)-2-thiophenecarboximidamide dihydrochloride (a) 2-Hydroxyethyl-7-nitro-1,2,3,4-tetrahydroisoquinoline hydrochloride To a solution of 7-nitro-1,2,3,4-tetrahydroisoquinoline hydrochloride (5.01 g, 23.3 mmol) in ethanol (200 ml) at 0° C. in a pressure bottle was added 2.5 M sodium hydroxide solution (10 ml). This solution was stirred for 0.2 h before ethylene oxide (4.2 ml) was added and the bottle was capped and the solution was stirred overnight while slowly allowing it to warm to ambient temperature. The solvent was concentrated and the aqueous solution was extracted twice with dichloromethane. The combined and dried (magnesium sulfate) extracts were concentrated to give an oil. This oil was immediately dissolved in ethanol (125 ml) and hydrochloric acid in ethanol was added until a distinctly acidic solution was obtained. After cooling, the title compound was collected and isolated as an off-white solid (3.76 g, 62%), m.p. 213° C. (dec.).

(b) 2-Hydroxyethyl-1,2,3,4-tetrahydroisoquinolin-7-amine hydrochloride

This compound was prepared by analogy with the method of Example 16 (d); from 2-hydroxyethyl-7-nitro-1,2,3,4-tetrahydroisoquinoline hydrochloride (2.0 g, 7.72 mmol) was isolated the title compound as an off-white solid (1.64 g, 93%), m.p. 181.5°3.5° C.

(c) N-(2-(2-Hydroxyethyl)-1,2,3,4-tetrahydroisoquinolin-7-yl)-2-thiophenecarboximidamide dihydrochloride This compound was prepared by analogy with the method of Example 5(b). From 2-hydroxyethyl-1,2,3,4-tetrahydroisoquinolin-1-amine hydrochloride (1.29 g, 5.64 mmol) was isolated after recrystallization from isopropanol 0.94 g (55%) of the free base as an off-white solid, m.p. 160–2.5° C. This was dissolved in isopropanol and acidified with hydrochloric acid in ethanol. The title compound was isolated as a white solid (1.08 g, 51%), m.p. 241–3° C.

EXAMPLE 19

N-(6,6a,7,8,9,10-Hexahydro-12H-pyrido[2,1-c][1,4] benzoxazepin-2-yl)-2-thiophenecarboximidamide dihydrochloride (a) 1-(2-Fluoro-5-nitrophenyl)methyl-2-(hydroxymethyl) piperidine hydrochloride To 2-fluoro-5-nitrobenzaldehyde (15 g) and 2-hydroxymethyl)piperidine (10.2 g) dissolved in methanol (150 ml) under nitrogen was added 8M borane-pyridine complex (11.1 ml). The reaction was stirred overnight. The reaction mixture was then evaporated in vacuo, and taken up in acidic water. The solution was washed with dichloromethane (2×150 ml), then made basic and extracted with dichloromethane (2×150 ml). The dichloromethane base extracts were combined, washed with water, dried and concentrated to provide a yellow oil (16.92 g). This oil was taken up in ethyl acetate and treated with saturated isopropanol-HCl, providing a white solid (14.2 g), m.p. 174–180° C. Recrystallization from a mixture of methanol, isopropanol and diethyl ether gave a white solid (4.88 g), m.p. 199–201° C.

(b) 2-Nitro-6,6a,7,8,9,10-hexahydro-12H-pyrido[2,1-c][1,4]benzoxazepine hydrochloride To 1-(2-fluoro-5-nitrophenyl)methyl-2-(hydroxymethyl)piperidine hydrochloride (4.88 g) in DMF (50 ml) under nitrogen was added 60% sodium hydride (1.41 g). The mixture was heated to 100° C. in an oil bath and stirred for 3 h. The resulting mix was diluted with water and extracted with ethyl acetate (3×200 ml). The combined extracts were washed with water, decolorized, dried and concentrated to yield a brown oil (4.62 g). The crude oil was chromatographed on silica eluting with 1:1 ethyl acetate-hexane. The product fractions were combined and concentrated to provide material (2.94 g) which was taken up in isopropanol, and treated with isopropanol-HCl until acidic. The resulting solids were collected by filtration to provide product (2.46 g), m.p. 250–252° C.

(c) 2-Amino-6,6a,7,8,9,10-hexahydro-12H-pyrido[2,1-c][1,4]benzoxazepine hydrochloride 2-Nitro-6,6a,7,8,9,10-hexahydro-12H-pyrido[2,1-c][1,4]benzoxazepine hydrochloride (2.46 g) dissolved in methanol (50 ml) was treated with 10% Pd-C (0.25 g), and hydrogenated on a Parr Hydrogenator for one hour, filtered and evaporated to yield a tacky solid (2.28 g).

(d) N-(6,6a,7,8,9,10-Hexahydro-12H-pyrido[2,1-c][1,4]benzoxazepin-2-yl)-2-thiophenecarboximidamide dihydrochloride Using the product from Example 19(c) (2.28 g), the title compound was obtained using the method of Example 1(d), 0.76 g, m.p. 276–278° C.

EXAMPLE 20

(+)-N-(1H,5H-2,3,11,11a-Tetrahydropyrrolo[2,1-c][1,4]benzoxazepin-7-yl)-2-thiophenecarboximidamide dihydrochloride m.p.>220° C. (dec.). This compound was prepared as for Example 19.

EXAMPLE 21

(−)-N-(1H,5H-2,3,11,11a-Tetrahydropyrrolo[2,1-c][1,4]benzoxazepin-7-yl)-2-thiophenecarboximidamide dihydrochloride m.p.>220° C. (dec.). This compound was prepared as for Example 19.

EXAMPLE 22

N-(2-Ethyl-2,3,4,5-tetrahydro-1,4-benzoxazapin-7-yl)-2-thiophenecarboximidamide dihydrochloride (a) 2-Ethyl-2,3,4,5-tetrahydro-1,4-benzoxazapine hydrochloride To 2-ethyl-2,3,4,5-tetrahydro-1,4-benzoxazapine-3,5-dione (10 g, 48.7 mmol) in anhydrous THF (100 ml) was added 1M borane in THF (390 ml, 390 mmol). The mixture was refluxed for 8 h, cooled to 0° C., and quenched by the dropwise addition of 4N HCl. The mixture was again brought to reflux for 1 h, concentrated on a rotovap, made basic with 50% NaOH, and extracted with ethyl acetate (3×100 ml). The combined extracts were washed with water, dried over magnesium sulfate, filtered, and concentrated to an oil. The oil was dissolved in isopropanol and treated with isopropanol-HCl. The salt was filtered off and dried in vacuo (8.0 g, 77%), m.p. 196–197° C.

(b) 7-Nitro-2-ethyl-2,3,4,5-tetrahydro-1,4-benzoxazapine hydrochloride

2-Ethyl-2,3,4,5-tetrahydro-1,4-benzoxazapine hydrochloride (8.0 g, 37.3 mmol) was dissolved in concentrated sulfuric acid (100 ml) and to this was added potassium nitrate (3.77 g, 37.3 mmol) at 0° C. The mixture was allowed to stir for 5 min, dumped into ice, neutralized with 50% NaOH, and extracted with ethyl acetate (3×100 ml). The combined extracts were washed with water, dried over magnesium sulfate, filtered, and concentrated to an oil. The oil was dissolved in isopropanol and treated with isopropanol-HCl. The salt was filtered off and dried in vacuo (4.4 g, 46%), m.p. 238–240° C.

(c) 7-Amino-2-ethyl-2,3,4,5-tetrahydro-1,4-benzoxazapine hydrochloride

7-Nitro-2-ethyl-2,3,4,5-tetrahydro-1,4-benzoxazapine hydrochloride (3.4 g, 13.1 mmol) was dissolved in methanol (100 ml) and hydrogenated at 50 psi in the presence of a catalytic quantity of 10% Pd-C. After 1 h the mixture was filtered through glass and evaporated to an oil which was used immediately in the next reaction.

(d) N-(2,3,4,5-Tetrahydro-1,4-benzoxazapin-7-yl)-2-thiophenecarboximidamide dihydrochloride The residue from the preceeding reaction was dissolved in 1-methyl-2-pyrrolidinone (20 ml) and to this was added S-methyl-2-thiophenethiocarboximide hydroiodide (3.81 g, 13.4 mmol). The mixture was stirred for 24 h at 45° C., dumped into basic water and extracted with ethyl acetate (3×100 ml). The combined extracts were washed with water, dried over magnesium sulfate, filtered, and concentrated to a solid which was recrystallized from ethyl acetate-methanol. The solid was dissolved in ethanol, treated with isopropanol-HCl and triturated with ether. The salt was collected by filtration (1.4 g, 31%), m.p.>260° C. (dec.).

EXAMPLE 23

N-(1-Methyl-2,3,4,5-tetrahydro-1H-1,4-benzoxazapin-7-yl)-2-thiophenecarboximidamide dihydrochloride (a) 7-Nitro-1-methyl-3,4-dihydro-1H-1,4-benzodiazapine-2,5-dione 1-Methyl-3,4-dihydro-1H-benzo[e][1,4]diazapine-2,5-dione (3.4 g, 17.9 mmol) was dissolved in concentrated sulfuric acid (30 ml) and to this was added potassium nitrate (1.95 g, 19.3 mmol) at 0° C. The mixture was stirred overnight, dumped onto ice, and the solids filtered off (3.62 g, 86%), m.p. 274–276° C.

(b) 7-Nitro-1-methyl-2,3,4,5-tetrahydro-1,4-benzoxazapine hydrochloride

To 7-nitro-1-methyl-3,4-dihydro-1H-1,4-benzodiazapine-2,5-dione (3.9 g, 16.6 mmol) in anhydrous THF (100 ml) was added 1M borane in THF (100 ml, 100 mmol). The mixture was refluxed for 5 h, cooled to 0° C., and quenched by the dropwise addition of 4N HCl. The mixture was again brought to reflux for 1 hr, concentrated to a rotovap, made basic with 50% NaOH, and extracted with ethyl acetate (3×100 ml). The combined extracts were washed with water, dried over magnesium sulfate, filtered, and concentrated to a solid. The solid was dissolved in ethanol and treated with isopropanol-HCl. The salt was filtered off and dried in vacuo (3.3 g, 85%), m.p.>260° C. (dec.).

(c) 7-Amino-1-methyl-2,3,4,5-tetrahydro-1H-1,4-benzoxazapine hydrochloride

7-Nitro-1-methyl-3,4-dihydro-1H-benzo[e][1,4] diazapine hydrochloride (3.2 g, 13.1 mmol) was dissolved in methanol (100 ml) and hydrogenated at 50 psi in the presence of a catalytic quantity of 10% Pd-C. After 1 h the mixture was filtered through glass and evaporated to an oil which was used immediately in the next reaction.

(d) N-(1-Methyl-2,3,4,5-tetrahydro-1H-1,4-benzodiazapin-7-yl)-2-thiophenecarboximidamide dihydrochloride The residue from the preceeding reaction was dissolved in 1-methyl-2-pyrrolidinone (10 ml) and to this was added S-methyl-2-thiophenethiocarboximide hydroiodide (3.60 g, 12.6 mmol). The mixture was stirred for 18 h at 45° C., dumped into basic water and extracted with ethyl acetate (3×100 ml). The combined extracts were washed with water, dried over magnesium sulfate, filtered, and concentrated to a solid which was recrystallized from ethyl acetate. The solid was dissolved in ethanol, treated with isopropanol-HCl and triturated with ether. The liquid was decanted and then more ether was added. The salt was collected by filtration, dissolved in water, and lyophilized (1.1 g, 26%), MS $(M+H)^+$ 288.

EXAMPLE 24

N-(3-Benzyl-1-methyl-2,3,4,5-tetrahydro-1,4-benzoxazapin-7-yl)-2-thiophenecarboximidamide dihydrochloride; m.p.>300° C. This compound was prepared as for Example 23.

EXAMPLE 25

N-(1-(N,N-Diethylamino)carbonylmethyl-1,2,3,4-tetrahydroisoquinolin-7-yl)-2-thiophenecarboximidamide fumarate (a) 2-(Phenylmethoxy)carbonyl-7-nitro-1,2,3,4-tetrahydroisoquinolin-1-acetic acid To a solution of 7-nitro-1,2,3,4-tetrahydroisoquinoline-1-acetic acid (5.0 g, 21.0 mmols) [Example 6(a)] in water (250 ml) at 0° C. was added 2M potassium hydroxide solution (15 ml). To this cooled solution was added in portions benzyl chloroformate (5.0 ml, 35 mmol) and the reaction mixture was stirred at 0° C. for 0.5 h. The solution was acidified with dilute hydrochloric acid and the precipitate which formed was collected. The dried solid was triturated with ether (200 ml) to give, after filtration, the title compound as a tan solid (4.83 g, 62%), m.p. 159.5–62° C.

(b) N,N-Diethyl-2-(phenylmethoxy)carbonyl-7-nitro-1,2,3,4-tetrahydroisoquinolin-1-acetamide To a stirred solution of 2-(phenylmethoxy)carbonyl-7-nitro-1,2,3,4-tetrahydroisoquinolin-1-acetic acid (5.0 g, 13.5 mmols), HOBT (1.8 g, 13.5 mmols) and TBTU (4.3 g, 13.5 mmols) in DMF (50 ml) was added diethylamine (13.5 mmols). To this was added slowly diisopropylethylamine (7.0 ml) and the reaction was then stirred for 48 h. The reaction was then poured into saturated NaCl and the aqueous phase then extracted with ethyl acetate (3×100 ml). The solvent was evaporated to leave a crude oil which was used as such.

(c) N,N-Diethyl-7-amino-1,2,3,4-tetrahydroisoquinolin-1-acetamide dihydrochloride To a pressure bottle charged with N,N-diethyl-2-(phenylmethoxy)carbonyl-7-nitro-1,2,3,4-tetrahydroisoquinolin-1-acetamide (10 mmols) dissolved in methanol (150 ml) and saturated methanol-HCl (20 ml) was added 10% Pd-C (250 mg), and the reaction was hydrogenated for 1 h. The catalyst was removed by filtration and the solvent evaporated to yield N,N-diethyl-7-amino-1,2,3,4-tetrahydroisoquinolin-1-acetamide dihydrochloride which was used as such in the next step.

(d) N-(1-(N,N-Diethylamino)carbonylmethyl-1,2,3,4-tetrahydroisoquinolin-4-yl)-2-thiophenecarboximidamide fumarate To a stirred solution of N,N-diethyl-7-amino-1,2,3,4-tetrahydroisoquinolin-1-acetamide dihydrochloride (14.7 mmols) in N-methylpyrrolidinone (50 ml) was added pyridine (1.27 g, 16.0 mmols). To the reaction was added S-methyl-2-thiophenethiocarboximide hydroiodide (3.65 g, 17.0 mmol) and the mixture was heated to 40° C. for 18 h. The reaction was then poured into 20% sodium hydroxide (300 ml). The aqueous phase was then extracted with ethyl acetate (3×100 ml), and dried over magnesium sulfate. Evaporation of the solvent yielded a crude oil. A fumaric acid salt was made using ethanol and isopropanol as solvents. The product, N-(1-(N,N-diethylamino)carbonylmethyl-1,2,3,4-tetrahydroisoquinolin-7-yl)-2-thiophenecarboximidamide fumarate was dried at 80° C. for 24 h (2.0 g), m.p. 189–190° C.

EXAMPLE 26

N-(1-Pyrrolidinylcarbonylmethyl-1,2,3,4-tetrahydroisoquinolin-7-yl)-2-thiophenecarboximidamide m.p. 163–164° C. This compound was prepared as for Example 25.

EXAMPLE 27

N-(1-Morpholinylcarbonylmethyl-1,2,3,4-tetrahydroisoquinolin-7-yl)-2-thiophenecarboximidamide bisfumarate m.p. 166–167° C. This compound was prepared as for Example 25.

EXAMPLE 28

N-(1-(((Ethyl)amino)carbonyl)methyl-1,2,3,4-tetrahydroisoquinolin-7-yl)-2-thiophenecarboximidamide bisfumarate m.p. 166–167° C. This compound was prepared as for Example 25.

EXAMPLE 29

N-(1-Piperidinylcarbonylmethyl-1,2,3,4-tetrahydroisoquinolin-7-yl)-2-thiophenecarboximidamide m.p. 134.5–7.5° C. This compound was prepared as for Example 25.

EXAMPLE 30

N-(2-(2-Hydroxyethyl)-2,3,4,5-tetrahydro-1H-2-benzazepin-8yl)-2-thiophenecarboximidamide fumarate (a) 2-(2-Hydroxyethyl)-8-nitro-2,3,4,5-tetrahydro-1H-2-benzazepine hydrochloride To a suspension of 8-nitro-2,3,4,5-tetrahydro-1H-2-benzazapine (5.08 g, 22.2 mmol) in ethanol (200 ml) at 0° C. was added 2.5M sodium hydroxide solution (10.0 ml). To this solution, in a pressure bottle, was added ethylene oxide (4.2 ml) and the bottle was capped and stirred at ambient temperature overnight. The solvent was concentrated in vacuo and the residue was partitioned between dichloromethane and dilute sodium hydroxide. The organic phase was dried (magnesium sulfate) and concentrated to give a yellow solid. This solid was taken up in ethanol and acidified with hydrochloric acid in ethanol. Addition of ether effected precipitation of the title salt as an orange solid (2.69 g, 44%). m.p. 193.5–4.5° C.

(b) N-(2-(2-Hydroxyethyl)-2,3,4,5-tetrahydro-1H-2-benzazepin-8-yl)-2-thiophenecarboximidamide fumarate To a solution of 2-(2-hydroxyethyl)-8 nitro-2,3,4,5-tetrahydro-1H-2-benzazapine hydrochloride (1.51 g, 5.54 mmol) in ethanol (100 ml) was added 10% Pd-C (0.2 g) and the solution was hydrogenated at 50 psi for 2 h. The reaction mixture was filtered and the filtrate was concentrated to give an oil. Evaporation with absolute ethanol gave 2-(2-hydroxyethyl)-2,3,4,5-tetrahydro-1H-2-benzazapin-8-amine hydrochloride as an amorphous solid (1.70 g, 110%) which was used without further purification. A solution of this salt (1.64 g, corrected to 1.50 g, 5.37 mmol) and S-methyl-2-thiophenethiocarboximide hydroiodide (1.91 g, 6.71 mmol) in N-methylpyrrolidinone (8.0 ml) was heated at 45° C. for 6 h. The reaction mixture was poured into water, basified, and extracted with dichloromethane. The dried (magnesium sulfate) organic phase was concentrated to give an oil. Column chromatography on silica gel, using 2% methanol in chloroform saturated with ammonia to 10% methanol in chloroform as agent, gave a yellow oil (1.69 g, 100%). This oil (1.02 g, 3.23 mmol) was dissolved in ethanol and fumaric acid (0.82 g, 7.91 mmol) was added and the solution was heated at reflux for 0.5 h. Upon cooling, the product was collected to give the monofumarate salt (0.68 g), m.p. 172–4° C.

EXAMPLE 31

(+)-N-(1,2,3,5,6,10b-Hexahydropyrrolo[2,1-a] isoquinolin-9-yl)-2-thiophenecarboximidamide (a) 1,2,3,5,6,10b-Hexahydropyrrolo[2,1-a]isoquinoline To a solution of 2,3,5,6-tetrahydro-1H-pyrrolo[2,1-a] isoquinolinium chloride (prepared by the method of S. Akaboshi, T. Kutsuma, and K. Achiwa, *J. Pharm. Bull.*, 1960, 8, 14, from N-(2-phenylethyl)-4-chlorobutyramide (56.4 g, 0.25 mol) and extracted into isopropanol-dichloromethane) in methanol (700 ml) and acetic acid (50 ml) at 0° C. was added portionwise sodium cyanoborohydride (19 g) over 1 h. After stirring overnight, the solvent was concentrated in vacuo. The residue was dissolved in dilute sodium hydroxide and was extracted twice with dichloromethane. The dried (magnesium sulfate) organic phase was concentrated to give an oil which was distilled using a Kugelrohr distilling apparatus, b.p. 100° C. at 0.25 mm, to give the title compound (30.4 g, 70%) as a pale yellow oil.

(b) 9-Nitro-1,2,3,5,6,10b-hexahydropyrrolo[2,1-a] isoquinoline hydrochloride

To concentrated sulfuric acid (200 ml) at −10° C. was added portionwise 1,2,3,5,6,10b-hexahydropyrrolo[2,1-a] isoquinoline (20.5 g, 118 mmol) over 2 h. After addition was complete, potassium nitrate (11.6 g, 0.115 mol) was added portionwise over 3 h. The reaction mixture was stirred for an additional 3 h and then poured onto ice and made basic with concentrated ammonium hydroxide. The product was extracted twice with dichloromethane. The dried (magnesium sulfate) organic phase was concentrated to give a red oil which was immediately dissolved in isopropanol (200 ml) and made acidic with saturated isopropanol-HCl. The resulting precipitate was collected to give a tan solid (18.9 g). Recrystallization from 95% ethanol (100 ml) afforded the title compound as an off-white solid (11.5 g, 62%), m.p. 243–5° C. This was converted to the free base by dissolving in water, making basic with dilute base, and extracting with dichloromethane to give 96% recovery of the product.

(c) (+)-9-Nitro-1,2,3,5,6,10b-hexahydropyrrolo[2,1-a] isoquinoline hydrochloride To a solution of 9-nitro-1,2,3,5,6,10b-hexahydropyrrolo [2,1-a]isoquinoline (12.2 g, 55.9 mmol) in methanol (400 ml) was added dibenzoyl-L-tartaric acid (21.8 g) and the solution was allowed to stir at ambient temperature overnight. The solid was collected to give material (16.0 g, 49.7%) with a 63.37 ratio of enantiomers as determined by chiral capillary zone electrophoresis (CE). This enriched salt was recrystallized several times from methanol to give the salt (5.4 g) with a 97:3 ratio of enantiomers. This salt (5.32 g, 9.21 mmol) was dissolved in water, made basic with dilute NaOH, and extracted twice with dichloromethane. The dried (magnesium sulfate) organic phase was concentrated to give an oil (2.09 g, 104%). This oil was taken up in ethanol (30 ml) and made acidic with ethanol-HCl to give the title compound as a white solid (1.99 g, 85%), m.p. 251–3° C. (dec.); $[\alpha]_D$+71.2° (c 1.0, MeOH). This salt was a 97:3 ratio of enantiomers by chiral CE.

(d) (+)-1,2,3,5,6,10b-Hexahydropyrrolo[2,1-a]isoquinolin-9-amine hydrochloride

A suspension (+)-9-nitro-1,2,3,5,6,10b-hexahydropyrrolo [2,1-a]isoquinoline hydrochloride (1.83 g, 7.18 mmol) and 10% Pd-C (0.2 g) in ethanol (150 ml) was hydrogenated at 50 psi for 0.75 h. The solution was filtered and the filtrate was concentrated to a volume of 25 ml. It was then heated to reflux to dissolve all of the solid and upon cooling the product precipitated. The title compound was isolated as a white solid (1.37 g, 85%), m.p. 239–41.5° C.; $[\alpha]_D$+62.5° (c 1.13, MeOH). This salt was a single enantiomer by chiral CE.

(e) (+)-N-(1,2,3,5,6,10b-Hexahydropyrrolo[2,1-a] isoquinolin-9-yl)-2-thiophenecarboximidamide A suspension of (+)-1,2,3,5,6,10b-hexahydropyrrolo[2,1-a]isoquinolin-9-amine hydrochloride (1.25 g, 5.56 mmol) and S-methyl-2-thiophenethiocarboximide hydroiodide (1.98 g, 6.94 mmol) in N-methylpyrrolidinone (4.0 ml) was heated at 45° C. for 4 h. The solution was poured into water and washed twice with ethyl acetate. The aqueous layer was basified with potassium carbonate and the crude product was collected to give a flocculent solid (1.55 g, 94%). Recrystallization from methanol-ethyl acetate gave the title compound as a yellow solid (1.07 g, 65%), m.p. 198.5–200.5° C.; $[\alpha]_D$+64.2° (c 1.01, MeOH). This salt was a single enantiomer by chiral HPLC.

EXAMPLE 32

(−)-N-(1,2,3,5,6,10b-Hexahydropyrrolo[2,1-a] isoquinolin-9-yl)-2-thiophenecarboximidamide (a) (−)-9-Nitro-1,2,3,5,6,10b-hexahydropyrrolo[2,1-a] isoquinoline hydrochloride The filtrate from Example 31(c) was concentrated in vacuo and converted to the free base by treatment with dilute sodium hydroxide. The resulting oil was taken up in methanol (250 ml) and dibenzoyl-D-tartaric acid (11.2 g) was added and the solution was allowed to stir at ambient temperature overnight. The solid was collected to give material (12.3 g, 38%) with a 26:74 ratio of enantiomers as determined by chiral CE. This enriched salt was recrystallized several times from methanol to give the salt (4.9 g) with a 2:98 ratio of enantiomers. This salt (4.74 g, 8.22 mmol) was dissolved in water, made basic with dilute NaOH, and extracted twice with dichloromethane. The dried (magnesium sulfate) organic phase was concentrated to give an oil (1.88 g, 105%). This oil was taken up in isopropanol (30 ml) and made acidic with isopropanol-HCl to give the title compound as a white solid (2.01 g, 96%), m.p. 250–2° C. (dec.); $[\alpha]_D$ –70.0° C. (c 1.07, MeOH). This salt was a 2:98 ratio of enantiomers by chiral CE.

(–)-1,2,3,5,6,10b-Hexahydropyrrolo[2,1-a]
isoquinolin-9-amine hydrochloride

This compound was prepared similarly to Example 31(d), (1.36 g, 82%), m.p. 240–3° C.; $[\alpha]_D$ –63.0° (c 1.05, MeOH). This salt was a single enantiomer by chiral CE.

(–)-N-(1,2,3,5,6,10b-Hexahydropyrrolo[2,1-a]
isoquinolin-9-yl)-2-thiophenecarboximidamide This compound was prepared similarly to Example 31(e), (0.97 g, 59%), m.p. 198–201° C.; $[\alpha]_D$ –65.5° (c 0.944, MeOH). The product was a single enantiomer by chiral HPLC.

N-(3,4,5,6,11,11a-Hexahydro-1H-[1,4]oxazino[4,3-b]isoquinolin-8-yl)-2-thiophenecarboximidamide (a) 7-Nitro-1,2,3,4-tetrahydro-3-isoquinolinecarboxylic acid methyl ester To concentrated sulfuric acid (200 ml), cooled in an ice bath, was added portionwise 1,2,3,4-tetrahydro-3-isoquinolinecarboxylic acid hydrochloride (20.4 g, 95.5 mmol). The mixture was stirred, with continued cooling, until the evolution of hydrogen chloride gas ceased. Then, potassium nitrate (9.8 g, 96.9 mmol) was added, in portions, whilst maintaining the temperature under 3° C. The mixture was stirred overnight, allowing it to come to room temperature, and then poured onto ice. Sodium acetate trihydrate (1.02 kg), dissolved in water, was then added to the resulting solution. Sufficient water was added to solubilize the salts; the final reaction volume was 5 l. The product was filtered off, washed with water and air dried, yield 17.35 g. NMR indicated this to be a mixture of the 7-nitro isomer (major component) and the 6-nitro isomer (minor component). This mixture was added to methanol (210 ml), the mixture acidified with dry hydrogen chloride, refluxed for 4 h and then allowed to cool with stirring. The product was filtered off, washed with methanol and air dried to yield 7-nitro-1,2,3,4-tetrahydro-3-isoquinolinecarboxylic acid methyl ester hydrochloride (12.9 g), pure by NMR. The hydrochloride salt was dissolved in water and the solution basified with concentrated ammonium hydroxide and stirred for 0.5 h. The solid was filtered off, washed with water and air dried to yield 7-nitro-1,2,3,4-tetrahydro-3-isoquinolinecarboxylic acid methyl ester (9.97 g), m.p. 133–5° C.

(b) 7-Nitro-1,2,3,4-tetrahydroisoquinoline-3-methanol

To 7-nitro-1,2,3,4-tetrahydro-3-isoquinolinecarboxylic acid methyl ester (5.0 g, 21.2 mmol) in dry tetrahydrofuran (18.5 ml) was added 10M borane-methyl sulfide complex (2.4 ml). The mixture was heated at reflux for 1.5 h while distilling off the methyl sulfide formed. The reaction mixture was cooled and methanol (2.7 ml) was added cautiously followed by 6N hydrochloric acid (5.4 ml). The mixture was then refluxed for 2.5 h and concentrated to dryness under reduced pressure. The solid residue was dissolved in water, the solution basified with 2.5N sodium hydroxide solution and the product extracted into dichloromethane. The crude product was purified by chromatography using silica gel and 5% methanol saturated with ammonia in dichloromethane to yield 7-nitro-1,2,3,4-tetrahydroisoquinoline-3-methanol (1.71 g).

(c) 2-Chloro-1-(3-hydroxymethyl-7-nitro-1,2,3,4-tetrahydroisoquinolin-2-yl)ethanone To a mixture of 7-nitro-1,2,3,4-tetrahydroisoquinoline-3-methanol (1.648 g, 7.92 mmol), dichloromethane (60 ml) and triethylamine (1.1 ml), cooled in an ice bath, was added chloroacetyl chloride (0.651 ml). The resulting solution was stirred overnight at room temperature. The reaction mixture was washed with dilute hydrochloric acid and then with water. The organic phase was dried over anhydrous magnesium sulfate and then concentrated under reduced pressure to yield 2-chloro-1-(3-hydroxymethyl-7-nitro-1,2,3,4-tetrahydroisoquinolin-2-yl)ethanone (2.08 g); MS 285 $(M+H)^+$.

(d) 8-Nitro-3,4,5,6,11,11a-hexahydro-1H-[1,4]oxazino[4,3-b]isoquinolin-4-one

To 2-chloro-1-(3-hydroxymethyl-7-nitro-1,2,3,4-tetrahydro-1H-isoquinolin-2-yl)ethanone (2.0 g, 7.03 ml) in tert-butanol (12 ml) was added potassium tert-butoxide (0.78 g). The mixture was then refluxed for 3 h. TLC indicated that the reaction was not complete. Additional potassium tert-butoxide (0.245 g) was added and heating continued for 0.5 h. Further potassium tert-butoxide (0.3 g) was added followed by 15 minutes of refluxing. At this point no starting material was detected by TLC. The mixture was cooled and dichloromethane (15 ml) was added. The insolubles were filtered off. The filtrate was concentrated under reduced pressure to yield 8-nitro-3,4,5,6,11,11a-hexahydro-1H-[1,4]oxazino[4,3-b]isoquinolin-4-one (0.7 g); MS 249 $(M+H)^+$.

(e) 8-Nitro-3,4,5,6,11,11a-hexahydro-1H-[1,4]oxazino[4,3-b]isoquinoline hydrochloride To a solution of 8-nitro-3,4,5,6,11,11a-hexahydro-1H-[1,4]oxazino[4,3-b]isoquinolin-4-one (0.7 g, 2.82 ml) in anhydrous tetrahydrofuran (10 ml) was added 1.0M borane in tetrahydrofuran (8.0 ml). The reaction mixture was heated at reflux for 3 h. After cooling to room temperature, the excess borane was quenched by the addition of methanol (2.0 ml) and then 2.5N hydrochloric acid (3.5 ml) was added and the mixture refluxed for 3.5 h. The reaction mixture was cooled to room temperature and the solid product filtered off and washed with tetrahydrofuran to give 8-nitro-3,4,5,6,11,11a-hexahydro-1H-[1,4]oxazino[4,3-b]isoquinoline hydrochloride (0.463 g), MS 235 $(M+H)^+$.

(f) 3,4,5,6,11,11a-Hexahydro-1H-[1,4]oxazino[4,3-b]isoquinolin-8-amine dihydrochloride To 8-nitro-3,4,5,6,11,11a-hexahydro-1H-[1,4]oxazino[4,3-b]isoquinoline hydrochloride (0.4 g) in methanol (50 ml) was added 6N hydrochloric acid (0.3 ml) and 5% Pd-C (100 mg). The mixture was treated with hydrogen at 50 psi on a Parr Hydrogenator. Hydrogen uptake was complete in 2.0 h. The catalyst was filtered off and the solvent removed under reduced pressure to yield the title product as a solid (0.4824 g).

(g) N-(3,4,5,6,11,11a-Hexahydro-1H-[1,4]oxazino[4,3-b]isoquinolin-8-yl)-2-thiophenecarboximidamide To a stirred mixture of 3,4,5,6,11,11a-hexahydro-1H-[1,4]oxazino[4,3-b]isoquinolin-8-amine dihydrochloride (0.461 g, 1.66 mmol) and methyl sulfoxide (5 ml) was added pyridine (0.28 ml) followed by S-methyl-2-thiophenethiocarboximide hydroiodide (0.612 g). The mixture was heated at 50° C., with stirring, for 4 h. The reaction mixture was then poured into water (50 ml) and after stirring for 1 hour, the mixture was clarified by filtration. The filtrate was basified with concentrated ammonium hydroxide to precipitate the product as a solid. The product was isolated, washed with water and dried; yield 0.4917 g, m.p. 190–4° C., MS 314 (M+H)+.

EXAMPLE 34

N-(2,3,4,6,11,11a-Hexahydro-1H-pyrazino[1,2-b]isoquinolin-8-yl)-2-thiophenecarboximidamide (a) 2-Chloroacetyl-7-nitro-1,2,3,4-tetrahydro-3-isoquinolinecarboxylic acid methyl ester To a mixture of 7-nitro-1,2,3,4-tetrahydro-3-isoquinolinecarboxylic acid methyl ester (Example 33 (a), 4.466 g, 18.9 mmol), dichloromethane (130 ml) and triethylamine (3.0 ml), cooled in an ice bath, was added dropwise chloroacetyl chloride (1.74 ml, 21.8 mmol). The resulting reaction mixture was stirred for 2 h at room temperature. The reaction mixture was then washed with dilute hydrochloric acid and then with water. The organic phase was dried over anhydrous magnesium sulfate and then concentrated under reduced pressure to yield 2-chloroacetyl-7-nitro-1,2,3,4-tetrahydro-3-isoquinolinecarboxylic acid methyl ester (6.22 g).

(b) 8-Nitro-3,6,11,11a-tetrahydro-2H-pyrazino[1,2-b]isoquinoline-1,4-dione

To a solution of 2-chloroacetyl-7-nitro-1,2,3,4-tetrahydro-3-isoquinolinecarboxylic acid methyl ester (6.22 g) in methanol (375 ml) in a stainless steel pressure vessel, cooled in a dry-ice bath, was added liquid ammonia (75 ml). The vessel was sealed and the bath removed. The contents were allowed to warm to room temperature overnight, with stirring. The solid product that formed was filtered off, washed with methanol and dried to give 8-nitro-3,6,11,11a-tetrahydro-2H-pyrazino[1,2-b]isoquinoline-1,4-dione (4.5 g), MS 262 (M+H)+.

(c) 8-Nitro-2,3,4,6,11,11a-hexahydro-1H-pyrazino[1,2-b]isoquinoline

To 8-nitro-3,6,11,11a-tetrahydro-2H-pyrazino[1,2-b]isoquinoline-1,4-dione (4.5 g, 17.2 mmol) in anhydrous tetrahydrofuran (100 ml) was added 1.0M borane in tetrahydrofuran (255 ml). The reaction mixture was heated at reflux for 6 h. After cooling to room temperature, the excess borane was quenched by the cautious addition of methanol (71 ml) and then 2.5N hydrochloric acid (71 ml). The mixture was then refluxed for 5 h. The reaction mixture was cooled to room temperature and concentrated to dryness under reduced pressure. The residue was dissolved in water, the solution basified with 2.5N sodium hydroxide and the product extracted into dichloromethane. The dark red solid (4.5 g) was purified by chromatography using silica gel and 5% methanol saturated with ammonia in dichloromethane to yield 8-nitro-2,3,4,6,11,11a-hexahydro-1H-pyrazino[1,2-b]isoquinoline (2.984 g), MS 234 (M+H)+.

(d) 2,3,4,6,11,11a-Hexahydro-1H-pyrazino[1,2-b]isoquinolin-8-amine trihydrochloride To 8-nitro-2,3,4,6,11,11a-hexahydro-1H-pyrazino[1,2-b]isoquinoline (2.98 g) in methanol (150 ml) and water (10 ml) was added concentrated hydrochloric acid (3.26 ml) and 5% Pd-C (300 mg). The mixture was treated with hydrogen at 50 psi on a Parr Hydrogenator. Hydrogen uptake was complete in 1.0 hour. The catalyst was filtered off and the solvent removed under reduced pressure to yield the title product as a solid (3.69 g).

(e) N-(2,3,4,6,11,11a-Hexahydro-1H-pyrazino[1,2-b]isoquinolin-8-yl)-2-thiophenecarboximidamide To a stirred mixture of 2,3,4,6,11,11a-hexahydro-1H-pyrazino[1,2-b]isoquinolin-8-amine trihydrochloride (1.8 g, 5.76 mmol) and methyl sulfoxide (20 ml) was added pyridine (0.94 ml) followed by S-methyl-2-thiophenethiocarboximide hydrochloride (2.13 g). The mixture was heated at 50° C., with stirring, for 7 h. The reaction mixture was then poured into water (150 ml) and, after stirring for 1 hour, the mixture was clarified by filtration. The filtrate was basified with 2.5N sodium hydroxide solution but no precipitate formed. An attempt to extract the product into dichloromethane caused the product to crystallize from the mixture. The product was isolated, washed with dichloromethane and dried; yield 1.28 g. This material was purified by chromatography using silica gel and 7% methanol saturated with ammonia in dichloromethane to yield N-(2,3,4,6,11,11a-hexahydro-1H-pyrazino[1,2-b]isoquinolin-8-yl)-2-thiophenecarboximidamide (0.83 g), m.p. 228° C. (dec.), MS 313 (M+H)+.

EXAMPLE 35

N-(1-Methyl-1,2,3,4-tetrahydroisoquinolin-7-yl)2-thiophenecarboximidamide dihydrochloride (a) 1-Methyl-7-nitro-3,4-dihydroisoquinoline 1-Methyl-3,4-dihydroisoquinoline (4.25 g, 29.3 mmol) was dissolved in ice cold concentrated sulfuric acid (15 ml) and to this was added potassium nitrate (3.25 g, 32.2 mmol) portionwise with cooling. The mixture was stirred overnight, poured over ice, basified with concentrated ammonium hydroxide, and the precipitated solid was collected, washed with water and dried: 4.47 g (80%), MS (M+H)+ 191, $^1$H NMR (D$_2$O), 8.30 (d, 1H), 8.22 (dd, 1H), 7.39 (d, 1H), 3.80–3.62 (m, 2H), 2.92–2.70 (m, 2H), 2.48 (broad s, 3H).

(b) 1-Methyl-7-nitro-1,2,3,4-tetrahydroisoquinoline hydrochloride

To a solution of 1-methyl-7-nitro-3,4-dihydroisoquinoline (397 g, 20.9 mmol) in methanol (80 ml) was added sodium borohydride (0.87 g, 23.0 mmol) portionwise. The mixture was stirred for 30 min., acidified with 6N HCl, the solvent was evaporated and the solid was stirred in isopropanol, collected and washed with ether: 5.33 g (>100%); MS (M+H)+ 193.

(c) 1-Methyl-1,2,3,4-tetrahydroisoquinolin-7-amine hydrochloride

A suspension of 1-methyl-7-nitro-1,2,3,4-tetrahydroisoquinoline hydrochloride (2.0 g, 8.75 mmol) in ethanol (100 ml) and a catalytic quantity of 10% Pd-C was hydrogenated until no more hydrogen was taken up. The catalyst was filtered off, the solvent was concentrated to a small volume, ether was added and the precipitated solid was collected and dried: 1.39 g (78%), MS (M+H)+ 163.

(d) N-(1-Methyl-1,2,3,4-tetrahydroisoquinolin-7-yl)-2-thiophenecarboximidamide dihydrochloride A solution of 1-methyl-1,2,3,4-tetrahydroisoquinolin-7-amine hydrochloride (0.50 g, 2.51 mmol) and S-methyl-2-thiophenecarboximide hydroiodide (0.89 g, 3.14 mmol) in N-methyl-2-pyrrolidinone (3 ml) was maintained at 60° C. for 3 h. The reaction mixture was poured into water, washed with two portions of ethyl acetate and basified with concentrated ammonium hydroxide. The product was extracted with two portions of ethyl acetate, dried (MgSO$_4$) and the solvent was evaporated giving a yellow syrup. This material was dissolved in isopropanol, acidified with a 95% ethanol-concentrated HCl mixture, diluted with ethyl acetate and left to crystallize in the freezer. The product was collected by filtration and dried in vacuo at 50° C. affording the title compound as a white solid (0.36 g, 42%); MS (M+H)+ 272; $^1$H NMR (D$_2$O) 8.04 (s, 1H), 7.65-7.30 (m, 5H), 4.73 (broad s, H$_2$+1H), 3.75-3.61 (m, 1H), 3.61-3.45 (m, 1H), 3.35-3.13 (m, 2H), 1.74 (d, 3H).

EXAMPLE 36

N-(1,2-Dimethyl-1,2,3,4-tetrahydroisoquinolin-7-yl)-2-thiophenecarboximidamide (a) 1,2-Dimethyl-7-nitro-1,2,3,4-tetrahydroisoquinoline hydrochloride A mixture of 1-methyl-7 nitro-1,2,3,4-tetrahydroisoquinoline (2.00 g, 8.75 mmol), formaldehyde (37% solution in water, 5 ml) and formic acid (9 ml) was heated at reflux for 2 h. The cooled solution was poured over ice, basified with concentrated ammonium hydroxide and extracted with two portions of chloroform. The dried ($MgSO_4$) solution was concentrated, the residue was dissolved in isopropanol, acidified with ethanolic HCl and left to crystallize. The product was collected and dried in vacuo affording a white solid (1.4 g, 67%); MS (M+H)$^+$ 207.

(b) 1,2-Dimethyl-1,2,3,4-tetrahydroisoquinolin-7-amine hydrochloride

This compound was prepared as described for Example 35(c). From 1,2-dimethyl-7-nitro-1,2,3,4-tetrahydroisoquinoline hydrochloride (1.30 g, 5.36 mmol) was isolated the title compound (1.01 g, 89%) as a white solid: MS (M+H)$^+$ 177.

(c) N-(1,2-dimethyl-1,2,3,4-tetrahydroisoquinolin-7-yl)-2-thiophenecarboximidamide This compound was prepared as described for Example 35(d). From 1,2-dimethyl-1,2,3,4-tetrahydroisoquinolin-7-amine hydrochloride (0.5 g, 2.35 mmol) was isolated, after recrystallization from ethyl acetate, the title compound (0.366 g, 55%), m.p. 168–70° C.

EXAMPLE 37

N-[1-(3-Methyl-1,2,4-oxadiazol-5-ylmethyl)-1,2,3,4-tetrahydroisoquinolin-7-yl]-2-thiophenecarboximidamide bismaleate A 60% dispersion of NaH (0.122 g, 3.04 mmol) was washed with two portions of hexane, suspended in THF (70 ml), acetamidoxime (0.25 g, 3.34 mmol) was added and the mixture was heated at reflux for 1 h. To the cooled mixture was added 3A molecular sieves (2 g) along with N-(1-methoxycarbonylmethyl-1,2,3,4-tetrahydroisoquinolin-7-yl)-2-thiophenecarboximidamide (Example 7, 0.5 g, 1.52 mmol), and the reaction was heated at reflux for 3 h. The reaction was cooled, the sieves were removed, water was added and the product was extracted with three portions of chloroform. After drying ($MgSO_4$), the solvent was removed, the residue was re-dissolved in isopropanol and acidified with maleic acid. The mixture was heated briefly to give a solution which was left to crystallize. The precipitated solid was collected by filtration, washed with ether and dried in vacuo affording the title compound (0.363 g, 41%) as a white solid, m.p. 151–3° C.

EXAMPLE 38

N-(1,2,3,5,10,10a-Hexahydropyrrolo[1,2-b]isoquinolin-7-yl)-2-thiophenecarboximidamide (a) 1,2,3,5,10,10a-Hexahydropyrrolo[1,2-b]isoquinoline A suspension of 2,3-dihydropyrrolo[1,2-b]isoquinolin-5 (1H)-one (10.8 g, 58.3 mmol) [G. M. Coppola, *J. Heterocycl. Chem.*, 181, 18, 767] in phosphorus oxychloride (100 ml) was heated at reflux for 1.5 h. Upon cooling, the solvent was removed in vacuo to give an oil. This oil was immediately taken up in cold methanol (275 ml) and sodium borohydride (4.0 g) was added portionwise to this solution while maintaining the reaction mixture at 0° C. The solvent was concentrated and the residue was dissolved in water and washed twice with ethyl acetate. The aqueous solution was made basic with potassium carbonate solution and extracted with ethyl acetate. The organic phase was dried (magnesium sulfate) and concentrated to give an oil. Column chromatography on silica gel gave unreacted starting material (3.57 g, 36%) and the title compound (4.2 g, 63% based on recovered starting material) as a light oil; MS 174 (M+H)$^+$; NMR (CDCl$_3$) 7.0–7.2 (broad m, 4H), 4.13 (d, 1H, J=15), 3.40 (d, 1H, J=15), 3.27 (dt, 1H), 2.9–3.1 (M, 1H), 2.71 (t, 1H), 1.4–2.4 (m, 6H).

(b) 7-Nitro-1,2,3,5,10,10a-hexahydropyrrolo[1,2-b]isoquinoline hydrochloride

To a solution of 1,2,3,5,10,10a-hexahydropyrrolo[1,2-b]isoquinoline (4.12 g, 23.8 mmol) in concentrated sulfuric acid (100 ml) at –10° C. was added, in portions over 1 h, potassium nitrate (2.40 g, 23.7 mmol). After addition was complete, the reaction mixture was stirred for 1 h before it was poured over ice. The aqueous solution was made basic with concentrated ammonium hydroxide and the product was extracted into dichloromethane (twice). The dried (magnesium sulfate) organic phase was concentrated to give a red oil that solidified on standing. This solid was taken up in isopropanol (100 ml) and hydrogen chloride in ethanol was added until acidic. The solid was collected, washed with isopropanol and dried to give the crude product (3.39 g, 56%). This solid was recrystalized from ethanol to give the title compound (2.16 g, 36%) as an off-white solid, m.p. 231–3° C. (dec.)

(c) 1,2,3,5,10,10a-Hexahydropyrrolo[1,2-b]isoquinolin-7-amine hydrochloride

To a suspension of 7-nitro-1,2,3,5,10,10a-hexahydropyrrolo[1,2-b]isoquinoline hydrochloride (2.14 g, 8.40 mmol) in methanol (150 ml) was added 10% Pd/C (0.2 g) and the reaction mixture was hydrogenated at 50 psi for 2 h. The solution was filtered and the catalyst was washed with water to dissolve some precipitated product. The filtrate was concentrated and absolute ethanol was used to help evaporate the excess water. The resulting solid was dissolved in hot ethanol (50 ml) and ether was added to precipitate the product. This solid was collected to give the title compound (1.90 g, 100%) as an amorphous, off-white solid, MS 189 (M+H)$^+$; NMR (DMSO-NaOD) 6.82 (d, 1H), 6.44 (d, 1H), 6.35 (s, 1H), 4.03 (d, 1H), 3.19 (broad s, 1H), 2.84 (d, 1H), 2.5–3.0 (m, 3H), 2.11 (broad s 1H), 2.7–2.9 (m, 2H), 1.52 (m, 1H).

(d) N-(1,2,3,5,10,10a-Hexahydropyrrolo[1,2-b]isoquinolin-7-yl)-2-thiophenecarboximidamide A solution of 1,2,3,5,10,10a-hexahydropyrrolo[1,2-b]isoquinolin-7-amine hydrochloride (0.81 g, 3.6 mmol) and S-methyl-2-thiophenethiocarboximide hydroiodide (1.28 g, 4.49 mmol) in N-methylpyrrolidinone (4.0 ml) was heated at 45° C. for 5 h. The reaction mixture was poured into water and extracted twice with ethyl acetate. The reaction mixture was then basified with dilute base and extracted thrice with dichloromethane. The combined extracts were dried (magnesium sulfate). Evaporation of the solvent gave the desired product in N-methylpyrrolidinone. Column chromatography on silica gel using 2% methanol in chloroform saturated with ammonia gas to 5% methanol in chloroform as eluent, gave the product (0.77 g, 72%). Recrystallization from ethyl acetate-hexanes gave the purified title compound (0.50 g, 40%) as a pale yellow solid, m.p. 171–3° C.

EXAMPLE 39

N-(1-Propyl-1,2,3,4-tetrahydroisoquinolin-7-yl)-2-thiophenecarboximidamide (a) 7-Nitro-1-propyl-1,2,3,4-tetrahydroisoquinoline hydrochloride To a solution of 1-propyl-3,4-dihydroisoquinoline (7.4 g, 42 mmol) [E. Späth, F. Berger, and W. Kuntara, *Chem. Ber.*, 1930, 63B, 134] in concentrated sulfuric acid (100 ml) at 0° C. was added in a single portion potassium nitrate (4.5 g, 45 mmol). The solution was allowed to slowly warm to ambient temperature overnight. The reaction mixture was poured onto ice and was basified with concentrated ammonium hydroxide. The resulting solid that formed in the cooled solution could not be filtered off satisfactorily. Hence, the reaction mixture was extracted twice with dichloromethane and the dried (magnesium sulfate) organic phases were concentrated in vacuo to give the intermediate 7-nitro-1-propyl-3,4-dihydroisoquinoline as an oil (8.78 g, 94%). This solid was taken up in methanol (200 ml), cooled to 0° C., and sodium borohydride (3.0 g) was added in portions over 0.5 h. After stirring for an additional 0.5 h, the reaction mixture was acidified to pH 5 using 6M hydrochloric acid. The solvent was concentrated at the rotoevaporator and the residue was partitioned between dichloromethane and dilute sodium hydroxide solution. The dried (magnesium sulfate) organic phase was concentrated to give the crude product as the free base. This was taken up in ethanol (200 ml) and hydrochloric acid in ethanol was added until acidic. The resulting solid which formed was collected to afford the title compound (5.60 g, 52%) as a pale yellow solid, m.p. 229–30.5° C. (dec.).

(b) 1-Propyl-1,2,3,4-tetrahydroisoquinolin-7-amine hydrochloride

To a suspension of 7-nitro-1-propyl-1,2,3,4-tetrahydroisoquinoline hydrochloride (2.51 g, 9.78 mmol) in ethanol (150 ml) was added 10% Pd-C (0.3 g) and the reaction mixture was hydrogenated at 50 psi for 3 h. The solution was filtered and the filtrate was concentrated and absolute ethanol was added to help evaporate any excess water. The resulting solid was triturated with isopropanol (30 ml) to give the title compound (1.42 g, 64%) as an off-white solid, m.p. 192–4° C.

(c) N-(1-Propyl-1,2,3,4-tetrahydroisoquinolin-7-yl)-2-thiophenecarboximidamide

A solution of 1-propyl-1,2,3,4-tetrahydroisoquinolin-7-amine hydrochloride (1.35 g, 5.95 mmol) and S-methyl-2-thiophenethiocarboximide hydroiodide (2.04 g, 7.15 mmol) in N-methylpyrrolidinone (5.0 ml) was heated at 45° C. for 6 h. The reaction mixture was poured into water and extracted twice with ethyl acetate. The reaction mixture was then basified with dilute potassium carbonate and extracted twice with ethyl acetate. The combined extracts were washed with water and dried (magnesium sulfate). Evaporation of the solvent gave an oil which solidified on standing. Recrystallization from ethyl acetate-hexanes gave the title compound (0.50 g, 29%) as a pale yellow solid, m.p. 127–8.5° C.

EXAMPLE 40

N-(2-Methyl-1-propyl-1,2,3,4-tetrahydroisoquinolin-7-yl)-2-thiophenecarboximidamide (a) 2-Methyl-7-nitro-1-propyl-1,2,3,4-tetrahydroisoquinoline hydrochloride A solution of 7-nitro-1-propyl-1,2,3,4-tetrahydroisoquinoline hydrochloride (2.50 g, 9.74 mmol) in formic acid (6.0 ml) and aqueous formaldehyde (9.0 ml) was heated at reflux for 1 h. The cooled solution was poured onto ice, made basic with concentrated ammonium hydroxide, and extracted with dichloromethane. The dried (magnesium sulfate) extracts were concentrated to give an oil which was taken up in ethanol and hydrochloric acid in ethanol was added until acidic. Since no precipitate formed on standing, the solvent was evaporated in vacuo and the residue was taken up in isopropanol (35 ml) and allowed to stand for several hours. The precipitate was collected to give the title compound (1.30 g, 49%) as an off-white solid, m.p. 198.5–200.5° C.

(b) 2-Methyl-1-propyl-1,2,3,4-tetrahydroisoquinolin-7-amine Hydrochloride

To a suspension of 2-methyl-7-nitro-1-propyl-1,2,3,4-tetrahydroisoquinoline hydrochloride (1.30 g, 4.80 mmol) in ethanol (100 ml) was added 10% Pd—C (0.2 g) and the reaction mixture was hydrogenated at 50 psi for 3 h. The solution was filtered and the filtrate was concentrated in vacuo. The residue was dissolved in isopropanol (30 ml) and allowed to stand overnight to give the title compound (1.04 g, 90%) as a tan solid, m.p. 217–9° C. (dec.).

(c) N-(2-Methyl-1-propyl-1,2,3,4-tetrahydroisoquinolin-7-yl)-2-thiophenecarboximidamide A solution of 2-methyl-1-propyl-1,2,3,4-tetrahydroisoquinolin-7-amino hydrochloride (1.01 g, 4.19 mmol) and S-methyl-2-thiophenethiocarboximide hydroiodide (1.43 g, 5.03 mmol) in N-methylpyrrolidinone (4.0 ml) was stirred at ambient temperature overnight. The reaction mixture was poured into water and extracted twice with ethyl acetate. The reaction mixture was then basified with dilute potassium carbonate solution and extracted twice with ethyl acetate. The combined extracts were washed with water and dried (magnesium sulfate). Column chromatography on silica gel using 2% methanol in chloroform saturated with ammonia gas as eluent, gave 1.39 g (105%) of the product. Trituration of the product several times with cyclohexane gave the purified title compound (1.02 g, 77%) as a pale yellow solid, m.p. 97–8.5° C.

EXAMPLE 41

N-(1-Ethyl-1,2,3,4-tetrahydroisoquinolin-7-yl)-2-thiophenecarboximidamide (a) N-(2-Phenylethyl)-propionamide The title compound was prepared in a reaction between phenethylamine (12.1 g, 100 mmol), propionyl chloride (9.25 g, 100 mmol) and triethylamine (20 ml) in methylene chloride (200 ml). The product (10.1 g) was used without purification; MS [M+H]$^+$ 178.

(b) 1-Ethyl-3,4-dihydroisoquinoline

A mixture of N-(2-phenylethyl)-propionamide (10 g, 56.4 mmol) and phosphorus pentoxide (80 g, 563 mmol) in tetralin (500 ml) was heated at reflux for 15 min, cooled, further phosphorus pentoxide (80 g) was added and reflux was resumed for 15 min. After standing overnight the tetralin was decanted, the residue was decomposed with ice-water, the suspension was filtered through celite and washed with two portions of ether. The aqueous solution was basified with concentrated ammonium hydroxide, extracted with three portions of ether, the extracts were dried (MgSO$_4$) and the solvent was evaporated giving a red solid (5.0 g, 55.7%); MS [M+H]$^+$ 160.

(c) 1-Ethyl-7-nitro-3,4-dihydroisoquinoline Hydrochloride

This compound was prepared as described for Example 41(a). From 1-ethyl-3,4-dihydroisoquinoline (5.0 g, 31.4 mmol) was isolated the title compound (3.31 g, 51.6%); MS [M+H]$^+$ 205.

(d) 1-Ethyl-7-nitro-1,2,3,4-tetrahydroisoquinoline Hydrochloride

This compound was prepared as described for Example 41(b). From 1-ethyl-7-nitro-3,4-dihydroisoquinoline hydrochloride (3.31 g, 16.2 mmol) was isolated the title compound (3.25 g, 82.7%); m.p. 260° C.; MS [M+H]$^+$ 207.

(e) 1-Ethyl-7-amino-1,2,3,4-tetrahydroisoquinoline Hydrochloride

This compound was prepared as described for Example 41(c). From 1-ethyl-7-nitro-1,2,3,4-tetrahydroisoquinoline hydrochloride (3.25 g, 13.4 mmol) was isolated the title compound (2.41 g, 84.5%); m.p. 150° C. (dec.); MS [M+H]$^+$ 177.

(f) N-(1-Ethyl-1,2,3,4-tetrahydroisoquinolin-7-yl)-2-thiophenecarboximidamide

This compound was prepared as described for Example 41(d) From 1-ethyl-7-amino-1,2,3,4-tetrahydroisoquinoline (500 mg, 2.94 mmol) was isolated the title compound after crystallization from cyclohexane (189 mg, 28%); m.p. 142–3.5° C., MS [M+H]$^+$ 286.

EXAMPLE 42

N-(1,3,4,6,11,11a-Hexahydro-2H-benzo[b]quinolizin-8-yl)carbamidothioic Acid, Ethyl Ester Bismaleate (a) 1-(1,3,4,6,11,11a-Hexahydro-2H-benzo[b]quinolizin-8-yl)thiourea To a solution of 1,3,4,6,11,11a-hexahydro-2H-benzo[b]quinolizin-8-amine hydrochloride (Example 16(d), 1.32 g, 5.53 mmol) in water (50 ml) was added dilute sodium hydroxide and the resulting solution was extracted twice with dichloromethane. The dried organic phase (magnesium sulfate) was concentrated to give the free base (1.18 g, 99%) as a solid. This solid was taken up in acetone (20 ml) and trifluoroacetic acid (0.63 g, 5.5 mmol) was added. This solution was heated to reflux and benzoylisothiocyanate (1.4 ml) was added. The reaction mixture was heated at reflux for 2 h and after cooling to ambient temperature the solid was collected to give the intermediate (1.97 g, 74%). This solid was taken up in methanol (25 ml) and 2.5M sodium hydroxide (10 ml) was added and the solution was heated at reflux for 1 h. The methanol was removed in vacuo and the aqueous solution was extracted three times with dichloromethane. The dried organic phase (magnesium sulfate) was concentrated to give the title compound as a white solid (1.07 g, 74%), m.p. 186.5–7.5° C. (dec).

(b) N-(1,3,4,6,11,11a-Hexahydro-2H-benzo[b]quinolizin-8-yl)carbamidothioic Acid, Ethyl Ester Bismaleate To a suspension of 2,3,4,6,11,11a-hexahydro-1H-pyrido[1,2-b]isoquinolin-8-yl)thiourea (1.06 g, 4.05 mmol) in isopropanol (10 ml) was added methanesulfonic acid (0.41 g, 4.3 mmol) in isopropanol (10 ml). The reaction mixture was heated at reflux for 0.5 h to ensure complete salt formation. To this solution was added ethyl methanesulfonate (1.4 ml) and heating was continued for 20 g to give a clear solution. The solvent was concentrated and the residue was dissolved in water, basified with dilute base and extracted into dichloromethane. The dried organic phase (magnesium sulfate) was concentrated. Column chromatography of the residue on silica gel, using 2% methanol in chloroform saturated with ammonia as eluent, gave the free base (0.96 g, 82%) as an off white solid. This solid was dissolved in isopropanol (20 ml) and maleic acid (0.85 g, 7.32 mmol) was added. The solution was heated to effect dissolution and after cooling overnight the title compound was isolated as a light tan solid (1.19 g, 56%), m.p. 145–7° C. (dec).

EXAMPLE 43

N-(1,2,3,5,10,10a-Hexahydro-1H-pyrrolo[1,2]isoquinolin-7-yl)carbamidothioic Acid, Ethyl Ester (a) 1-(1,2,3,5,10,10a-Hexahydropyrrolo[2,1-b]isoquinolin-7-yl)-2-thiourea 1,2,3,5,10,10a-Hexahydropyrrolo[1,2-b]isoquinolin-7-amine hydrochloride (Example 38(c), 1.04 g, 4.63 mmol) was dissolved in water, basified with dilute sodium hydroxide and extracted twice with dichloromethane. The solution was filtered and the solvent was concentrated to give the free base as a solid (0.86 g, 99%). This was taken up in acetone (25 ml) and trifluoroacetic acid (0.52 g, 4.6 mmol) in acetone (10 ml) was added. The reaction mixture was heated to reflux and benzoyl isothiocyanate (1.2 ml) was added in a single portion and heating was continued for 1 h. The solid was collected to give the intermediate as a white solid (1.24 g, 57%). The filtrate showed the presence of mainly desired intermediate and the solvent was removed in vacuo. To the residue thus obtained was added the intermediate white solid and the mixture was taken up in methanol (30 ml) and 2.5M sodium hydroxide (10 ml). The solution was heated at 95° C. for 1 h. Upon evaporation of the methanol under reduced pressure, the product precipitated. This solid was collected and washed with water to give, after drying in air, the title compound as a pale yellow solid (0.89 g, 77%), m.p. 192–3° C. (dec).

(b) N-(1,2,3,5,10,10a-Hexahydro-1H-pyrrolo[1,2-b]isoquinolin-7-yl)carbamidothioic Acid, Ethyl Ester To a suspension of 1-(1,2,3,5,10,10a-hexahydropyrrolo[2,1-b]isoquinolin-7-yl)-2-thiourea (0.86 g, 3.5 mmol) in isopropanol (8 ml) was added methanesulfonic acid (0.34 g, 3.6 mmol) in isopropanol (8 ml). The resulting solution was heated at reflux for 0.5 h to ensure complete salt formation. To the reaction mixture was added ethyl methanesulfonate (1.3 ml) and heating was continued overnight to give a cheer colorless solution. The solvent was removed in vacuo and the residue was dissolved in water, basified with potassium carbonate, and extracted with ethyl acetate. The organic phase was washed with water, dried over magnesium sulfate and concentrated in vacuo. The solid was taken up in an equal volume of ether and cyclohexane. This solution was treated with decolorizing carbon, filtered and evaporated in vacuo. Trituration of this solid with a minimum amount of cyclohexane gave the title compound as an off-white solid (0.60 g, 63%), m.p. 98–101° C.

EXAMPLE 44

N-(1,2,3,5,6,10b-Hexahydropyrrolo[2,1-a]isoquinolin-9yl)carbamidothioic Acid, Ethyl Ester (a) 9-Amino-1,2,3,5,6,10b-hexahydropyrrolo[2,1-a]isoquinoline To 9-nitro-1,2,3,5,6,10b-hexahydropyrrolo[2,11-a]isoquinoline hydrochloride (Example 31(b), 2.0 g) in methanol (100 ml) was added concentrated hydrochloric acid (0.67 ml) and 5% palladium on carbon (200 mg). The mixture was hydrogenated at 50 psi on a Parr Hydrogenator. Hydrogen uptake was complete in 1.0 h. The catalyst was filtered off and the solvent removed under reduced pressure. The residue was dissolved in water, the solution basified with 2.5M sodium hydroxide and the product extracted into dichloromethane. The extracts were dried over anhydrous magnesium sulfate and the solvent removed under reduced pressure to yield the title compound as a thick oil (1.55 g).

(b) 1-(1,2,3,5,6,10b-Hexahydropyrrolo[2,1-a]isoquinolin-9yl)-2-thiourea

To 9-amino-1,2,3,5,6,10b-hexahydropyrrolo[2,1-a]isoquinoline (1.48 g, 7.85 mmol) in acetone (28 ml) was added trifluoroacetic acid (0.894 g, 7.85 mmol) in acetone (28 ml). This mixture was heated to a gentle reflux and benzoylisothiocyanate (1.99 ml) was added. The reaction mixture was heated to reflux for 3.5 h and after cooling to ambient temperature the solid was collected to give the intermediate (2.14 g). This solid was taken up in methanol (25 ml) and 2.5M sodium hydroxide (10 ml) was added and the solution was heated at reflux for 1.5 h. The reaction mixture was cooled to room temperature and the solid collected and washed with water. The methanol was removed from the filtrate and the solid collected from the aqueous slurry. The total yield of the title compound, as a white solid, was 1.04 g, m.p. 185–7° C. (dec.); MS (M+H)$^+$ 248.

(c) N-(1,2,3,5,6,10b-Hexahydropyrrolo[2,1-a]isoquinolin-9-yl)carbamidothioic Acid, Ethyl Ester To a stirred mixture of 1-(1,2,3,5,6,10b-hexahydropyrrolo[2,1-a]isoquinolin-9yl)-2-thiourea (1.0 g, 4.04 mmol) and ethanol (20 ml) was added methanesulfonic acid (0.262 ml, 4.04 mmol). The mesylate salt precipitated. After stirring for a few minutes, ethyl methanesulfonate (1.3 ml) was added. The reaction mixture was refluxed, with stirring for 22 h. Thin layer chromatography indicated that the reaction was only 50% complete. Addition of ethyl methanesulfonate (0.5 ml) and refluxing for another 22 h drove the reaction to completion. The solution was concentrated under reduced pressure. The residue was dissolved in water, the solution basified with sodium carbonate solution and the product isolated by extraction into dichloromethane. The crude product was purified by chromatography using silica gel and 5% methanol saturated with ammonia in dichloromethane. The chromatographed material was dissolved in hot ethyl acetate, the solution clarified, and then concentrated to dryness. This was repeated using cyclohexane. The product was then triturated in a small amount of hot ether, the mixture cooled and the product isolated (0.382 g); m.p. 116–7° C.; MS (M+H)$^+$ 276.

EXAMPLE 45

(+)-N-2,3,4,11,11a-Tetrahydro-1H,5H-pyrrolo[2,1-c][1,4]benzoxazepin-7-yl)carbamidothioic Acid, Ethyl Ester Bismaleate (a) 1-((2-Fluoro-5-nitrophenyl)methyl)-pyrrolidin-2-methanol Hydrochloride To 2-fluoro-5-nitrobenzaldehyde (20 g, 118 mmol) in absolute ethanol (200 ml) was added (R)-(−)-2-pyrrolidinemethanol (21 g, 118 mmol) and 8M borane-pyridine complex (15 ml, 118 mmol). The mixture was stirred for 24 h, concentrated, dissolved in acidic water, and extracted with dichloromethane (2×100 ml). The combined extracts were washed with water, dried over magnesium sulfate, filtered, and concentrated to a oil. The oil was dissolved in isopropanol and treated with isopropanol-HCl. The salt was collected by filtration (15.2 g, 46%), m.p. 147–149° C.

(b) 7-Nitro-2,3,4,11,11a-tetrahydro-1H,5H-pyrrolo[2,1-c][1,4]benzoxazepine Hydrochloride To 1-((2-Fluoro-5-nitrophenyl)methyl)-pyrrolidin-2-methanol (1.97 g, 6.77 mmol) in DMSO (30 ml) was added 25% NaOH (3.25 g). The mixture was stirred for 1 h, dumped into water, and the solids filtered off. The solids were washed with water, dried in vacuo, dissolved in isopropanol, treated with isopropanol-HCl, and the salt filtered off (1.41 g, 77%), m.p. 253–255° C.

(c) 7-Amino-2,3,4,11,11a-tetrahydro-1H,5H-pyrrolo[2,1-c][1,4]benzoxazepine

7-Nitro-2,3,4,11,11a-tetrahydro-1H,5H-pyrrolo[2,1-c][1,4]benzoxazepine (3.07 g, 11.0 mmol) was dissolved in methanol (50 ml) and hydrogenated at 50 psi in the presence of a catalytic quantity of 10% Pd—C. After 1 h the mixture was filtered through glass and evaporated to a solid (2.79 g, 100%), m.p. 64–67° C.

(d) 1-Benzoyl-3-(2,3,4,11,11a-tetrahydro-1H,5H-pyrrolo[2,1-c][1,4]benzoxazepine-7-yl)thiourea To 7-amino-2,3,4,11,11a-tetrahydro-1H,5H-pyrrolo[2,1-c][1,4]benzoxazepine (9.0 g, 44.1 mmol) in acetone (150 ml) was added benzoyl isothiocyanate (14.4 g, 88.2 mmol). The mixture was brought to reflux, maintained for 0.5 h, cooled, and evaporated. The oil was dissolved in dichloromethane and washed with water. The organic layer was dried over magnesium sulfate, filtered, and concentrated to a oil which was used immediately in the next reaction.

(e) (2,3,4,11,11a-Tetrahydro-1H,5H-pyrrolo[2,1-c][1,4]benzoxazepine-7-yl)thiourea To the crude material from the preceeding reaction, dissolved in methanol (100 ml), was added 2N NaOH (40 ml) and the mixture brought to reflux (1 h). The methanol was evaporated off and the aqueous phase extracted with ethyl acetate (3×100 ml). The combined extracts were washed with water, dried over magnesium sulfate, filtered, concentrated, and chromatographed over silica gel eluting with 5% methanol in chloroform to yield a glassy solid (3.31 g, 28%, two steps).

(f) (+)-N-2,3,4,11,11a-Tetrahydro-1H,5H-pyrrolo[2,1-c][1,4]benzoxazepin-7-yl)carbamidothioic Acid, Ethyl Ester Bismaleate To (2,3,4,11,11a-tetrahydro-1H,5H-pyrrolo[2,1c][1,4]benzoxazepine-7-yl)thiourea (3.31 g, 12.6 mmol) in ethanol (20 ml) was added methanesulfonic acid (0.815 ml, 12.6 mmol) followed by ethyl methanesulfonate (1.74 ml, 16.4 mmol). The mixture was heated under reflux for 10 h (an additional equivalent of ethyl methanesulfonate was added during this period), cooled, and evaporated. The remaining oil was dumped into water, made basic with 2N NaOH, and extracted with ethyl acetate (3×100 ml). The combined extracts were washed with water, dried over magnesium sulfate, filtered, and concentrated to a solid which was recrystallized from ethyl acetate-hexane. The solid was dissolved in ethanol and treated with 2.1 equivalents of maleic acid. After trituration with ether solids formed (1.17 g, 18%), m.p. 123–124° C.; [α]$_D$+29.4° (c 1.162, methanol).

What is claimed is:

1. A compound of formula (I)

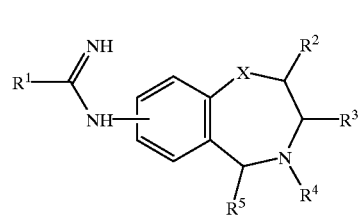

wherein:

X represents NR$^6$;

R$^1$ represents S-alkyl C1 to 3 or a five membered heterocyclic aromatic ring containing 1 to 4 heteroatoms selected from O, N and S optionally substituted at a carbon atom by one or more groups selected from halogen, trifluoromethyl, alkyl C1 to 6, nitro, or cyano;

R$^2$ represents hydrogen, alkyl C1 to 6, —(CH$_2$)$_d$OH, —(CH$_2$)$_d$OAr or —(CH$_2$)$_n$Ar;

R$^3$ represents hydrogen, alkyl C1 to 6, —(CH$_2$)$_b$OH, —(CH$_2$)$_b$OAr or —(CH$_2$)$_n$Ar;

R⁴ represents hydrogen, alkyl C1 to 6, —(CH₂)_cOH, —(CH₂)_cOAr or —(CH₂)_hAr;

R⁵ represents hydrogen, alkyl C1 to 6, —(CH₂)_qOH, —(CH₂)_qOAr or —(CH₂)_nAr; —(CH₂)_tCOOR⁸ or —(CH₂)_tCONR⁹R¹⁰;

or either R³ and R⁴ together or R⁴ or R⁵ together represent a chain —(CH₂)_m— or (CH₂)_rY(CH₂)_p—;

Ar represents a phenyl ring, a six membered heterocyclic aromatic ring containing one or two nitrogen atoms, or a five membered heterocyclic aromatic ring containing 1 to 4 heteroatoms selected from O, N and S, which phenyl ring, six membered heterocyclic aromatic ring or five membered heterocyclic aromatic ring may be optionally substituted by one or more groups selected from alkyl C1 to 6, alkoxy C1 to 6, halogen, nitro, cyano, perfluoroalkyl C1 to 6, phenyl or a five membered heterocyclic aromatic ring containing 1 to 4 heteroatoms selected from O, N and S;

Y represents O, S or NR⁷;

m represents an integer 3 to 5;

r and p independently represent integers 1 to 3 save that r+p shall be in the range 2 to 4;

R⁶, R⁷, R⁸, R⁹ and R¹⁰ independently represent hydrogen or alkyl C1 to 6;

or —NR⁹R¹⁰ together represent piperidinyl, pyrrolidinyl, morpholinyl, tetrahydroisoquinolinyl, piperazinyl, or piperazinyl-4-substituted by group R¹⁵;

R¹⁵ represents alkyl C1 to 6 or a group —(CH₂)_wQ;

Q represents phenyl optionally substituted by one or more groups selected from alkyl C1 to 6, alkoxy C1 to 6, halogen, nitro, cyano and trifluoromethyl;

n and w independently represent an integer 0 to 6;

d represents an integer 1 to 6;

h, q and b independently represent an integer 1 to 6;

c represents an integer 2 to 6;

t represents an integer 1 to 5;

provided that when X represents NH, and at the same time R², R³ and R⁵ each represent hydrogen, than R⁴ does not represent hydrogen or alkyl C1 to 6;

and optical isomers and racemates thereof and pharmaceutically acceptable salts thereof.

2. A compound of formula (I), according to claim 1, wherein R¹ represent S-alkyl C1 to 3 or a ring containing one heteroatom selected from O, N and S.

3. A compound of formula (I), according to claim 2, wherein R¹ represents thienyl.

4. A compound of formula (I), according to claim 3, wherein R¹ represents 2-thienyl.

5. A compound of formula (I), according to claim 2, wherein R¹ represents S-ethyl.

6. A pharmaceutical formulation comprising a compound of formula (I), as defined in claim 1, or an optical isomer or racemate thereof or a pharmaceutically acceptable salt thereof, optionally in admixture with a pharmaceutically acceptable diluent or carrier.

7. A method of treating human diseases or conditions in which inhibition of nitric oxide synthase activity is beneficial which comprises administering to a person suffering from such a disease or condition, a therapeutically effective amount of a compound of formula (I), as defined in claim 1, or an optical isomer or racemate thereof or a pharmaceutically acceptable salt thereof.

8. A method of treatment according to claim 7 in which it is predominantly the neuronal isoform of nitric oxide synthase that is inhibited.

9. A method of treating hypoxia or stroke or ischaemia or neurodegenerative conditions to schizophrenia or pain or migraine or for the prevention and reversal of tolerance to opiates and diazepines which comprises administering to a person suffering from to such a disease or condition a therapeutically effective amount of a compound of formula (I) as defined in claim 1, or an optical isomer or racemate thereof or a pharmaceutically acceptable salt thereof.

10. A method of treatment according to claim 9, wherein the condition to be treated is selected from the group consisting of hypoxia, ischaemia, stroke, Amyotrophic Lateral Sclerosis and pain.

11. A method of treatment according to claim 10, wherein the condition to be treated is stroke.

12. A method of treatment according to claim 10, wherein the condition to be treated is Amyotrophic Lateral Sclerosis.

13. A method of treatment according to claim 10, wherein the condition to be treated is pain.

14. A process for the preparation of a compound of formula (I), as defined in claim 1, and optical isomers and racemates thereof and pharmaceutically acceptable salts thereof, which comprises:

(a) preparing a compound of formula (I) by reacting a corresponding compound of formula (II)

(II)

wherein X, R², R³, R⁴ and R⁵ are as defined in claim 1, with a compound of formula (III)

(III)

wherein R¹ is as defined in claim 1 and L is a leaving group;

(b) preparing a compound of formula (I) by reacting a corresponding compound of formula (IV)

(IV)

wherein X, R², R³, R⁴ and R⁵ are as defined in claim 1 and HA is an acid, with a compound of formula (V)

R¹—≡N (V)

wherein R¹ is as defined in claim 1;

(c) preparing a compound of formula (I) wherein R¹ is S-alkyl C1 to 3 by reacting a corresponding compound of formula (VI)

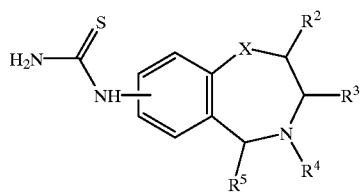 (VI)

wherein X, $R^2$, $R^3$, $R^4$ and $R^5$ are as defined in claim 1, with a compound of formula (VII)

$$R^1—L \quad (VII)$$

wherein $R^1$ is alkyl C1 to 3 and L is a leaving group;

(d) preparing a compound of formula (I) in which $R^4$ represents alkyl C1 to 6, —$(CH_2)_cOH$, —$(CH_2)_cOAr$ or —$(CH_2)_nAr$ by reacting a corresponding compound of formula (I) in which $R^4$ represents hydrogen with a compound of formula (VIII)

$$R^{11}—L \quad (VIII)$$

wherein $R^{11}$ represents alkyl C1 to 6, —$(CH_2)_cOH$, —$(CH_2)_cOAr$ or —$(CH_2)_nAr$ and L is a leaving group;

(e) preparing a compound of formula (I) in which X represents $NR^6$ and $R^6$ represents alkyl C1 to 6 by reacting a corresponding compound of formula (I) in which $R^6$ represents hydrogen with a compound of formula (IX)

$$R^{12}—L \quad (IX)$$

wherein $R^{12}$ represents alkyl C1 to 6 and L is a leaving group;

(f) preparing a compound of formula (I) in which $R^3$ and $R^4$ or $R^4$ and $R^5$ are joined to form a chain —$(CH_2)_r$$Y(CH_2)_p$—, Y represents $NR^7$ and $R^7$ represents alkyl C1 to 6 by reacting a corresponding compound of formula (I) in which $R^7$ represents hydrogen with a compound of formula (IX);

(g) preparing a compound of formula (I) in which $R^5$ represents —$(CH_2)_tCOOR^8$ and $R^8$ represents alkyl C1 to 6 by esterifying a corresponding compound of formula (I) in which $R^8$ represents hydrogen;

(h) preparing a compound of formula (I) in which $R^5$ represents —$(CH_2)_tCOOR^8$ and $R^8$ represents hydrogen by hydrolysing a corresponding compound of formula (I) in which $R^8$ represents alkyl C1 to 6;

(i) preparing a compound of formula (I) in which $R^5$ represents —$(CH_2)_tCONR^9R^{10}$ and $R^9$ and/or $R^{10}$ represents alkyl C1 to 6 by alkylating a corresponding compound of formula (I) in which $R^9$ and/or $R^{10}$ represents hydrogen;

(j) preparing a compound of formula (I) in which $R^5$ represents —$(CH_2)_tCONR^9R^{10}$ in which $R^9$ and $R^{10}$ represent hydrogen or $R^5$ represents —$(CH_2)_tCOOR^8$ and $R^8$ represents hydrogen by hydrolysis of the corresponding cyano compound;

(k) preparing a compound of formula (I) in which $R^5$ represents —$(CH_2)_tCONR^9R^{10}$ by reacting the corresponding amine $HNR^9R^{10}$ with the corresponding acid;

(l) preparing a compound of formula (I) in which $R^2$ represents —$(CH_2)_dOAr$, $R^3$ represents —$(CH_2)_bOAr$, $R^4$ represents —$(CH_2)_cOAr$ or $R^5$ represents —$(CH_2)_qOAr$ by reacting the corresponding halo or sulphonate compound of formula (I) with an aryl hydroxide;

(m) preparing a compound of formula (I) in which $R^4$ represents methyl by reacting a corresponding compound of formula (I) in which $R^4$ represents hydrogen with formaldehyde and formic acid; or (n) preparing a compound of formula (I) in which $R^4$ represents —$CH_2CH_2OH$ by reacting a corresponding compound of formula (I) in which $R^4$ represents hydrogen with oxirane;

and where desired or necessary converting the resultant compound of formula (I), or another salt thereof, to a pharmaceutically acceptable salt thereof, or vice versa.

15. A compound of formula (I) which is:

(−)-N-(10-methyl-2,3,5,10,11,11a-hexahydro-1H-pyrrolo[2,1-c][1,4]benzodiazapin-7-yl)-2-thiophenecarboximidamide;

N-(1-methyl-2,3,4,5,tetrahydro-1H-1,4-benzodiazapin-7-yl)-2-thiophenecarboximidamide;

N-(3-benzyl-1-methyl-2,3,4,5,tetrahydro-1H-1,4-benzodiazapin-7-yl)-2-thiophenecarboximidamide; or an optical isomer or racemate of any one thereof or a pharmaceutically acceptable salt of any one thereof.

16. A method of treatment according to claim 7, wherein the condition to be treated is Parkinson's Disease.

17. A method of treatment according to claim 7, wherein the condition to be treated is schizophrenia.

18. A method of treatment according to claim 9, wherein the condition to be treated is migraine.

* * * * *